US 6,317,719 B1

(12) United States Patent
Schrier et al.

(10) Patent No.: US 6,317,719 B1
(45) Date of Patent: Nov. 13, 2001

(54) PROVIDING PATIENT-SPECIFIC DRUG INFORMATION

(75) Inventors: Robert W. Schrier, Englewood, CO (US); John G. Gambertoglio; Francesca T. Aweeka, both of Burlingame, CA (US); Douglas M. Schrier, Denver, CO (US); Janet L. Austin, Castle Rock, CO (US); Cheryl D. Heiland, Highlands Ranch, CO (US); Timothy J. McNamara, Lakewood, CO (US)

(73) Assignee: Cerner Mulium, Inc., Denver, CO (US)

( * ) Notice: Subject to any disclaimer, the term of this patent is extended or adjusted under 35 U.S.C. 154(b) by 0 days.

(21) Appl. No.: 09/189,731

(22) Filed: Nov. 10, 1998

Related U.S. Application Data

(63) Continuation of application No. 08/629,763, filed on Apr. 9, 1996, now Pat. No. 5,833,599, which is a continuation of application No. 08/167,286, filed on Dec. 13, 1993, now abandoned.

(51) Int. Cl.[7] .................................................. G06F 17/60
(52) U.S. Cl. ........................ 705/2; 705/2; 705/3; 705/4; 604/31
(58) Field of Search .................. 705/2, 3, 4; 378/87; 604/31

(56) References Cited

U.S. PATENT DOCUMENTS 4,839,806 * 6/1989 Goldfischer et al. ................. 378/87
5,088,981 * 2/1992 Howson et al. ........................ 604/31

OTHER PUBLICATIONS

Micromedix, Inc. Knowledge bases for healthcare, Safety & the Environment, Sep. 1974.*
Gannon, Kathi, Prescription drugs, PP 1–2, Feb. 1995.*
Gurwitz et al, Antihypertensive Drug–therapy and the initiation of treatment for diabetes, PP 1, Feb. 1993.*
Sauders et al, assessing the feasibility of using computerized pharmacy refill data, PP 1, Oct. 1998.*
Kuschner, Nonprescription bronchodilator medication use in asthma, PP 1, Oct. 1997.*
Anogianakis et al, Computer–aided prescription–a prototype system, PP 1, 1997.*
Gardner et al., "A strategy for development of computerized critical care decision support systems," *Journal of Clinical Monitoring and Computing*, 8: 263–269, 1992.
Glaser, Ph.D. et al., "The future of clinical information systems: One hospital's perspective," *The Future of Clinical Information Systems*, 12–24, Aug. 1993.

(List continued on next page.)

Primary Examiner—James P. Trammell
Assistant Examiner—Mussie Tesfamariam
(74) Attorney, Agent, or Firm—Fish & Richardson, P.C.

(57) ABSTRACT

Systems and methods for processing data relating to use of a drug by a patient that receive patient information and determine a dosage of the drug on the basis of the patient information. The systems and methods may be operated to provide patient-specific information on drug cost and on comparative costs of alternative drugs, on side effects, on allergies, and on pharmacology, as well as information on use in pregnancy, on use in lactation, on drug interactions, on warnings and contraindications, and supporting references. The systems may also be operated to prepare drug orders and prescriptions.

16 Claims, 22 Drawing Sheets

OTHER PUBLICATIONS

Goldberg et al., "Computer–based program for identifying medication orders requiring dosage modification based on renal function," *American Journal of Hospital Pharmacy*, vol. 48, Sep. 1991, 6 pgs.

Halpern et al., "A Computerized Intensive Care Unit Order–Writing Protocol," *The Annals of Pharmacotherapy*, vol. 26, Feb. 1992, 5 pgs.

Lepage MD, et al., "Assessing the Effectiveness of a Computerized Blood Order Consultation System," AMIA, Inc., 1992, 33–37.

McDonald MD, et al., "The Medical Gopher–A Microcomputer System to Help Find, Organize and Decide About Patient Data," *The Western Journal of Medicine*, vol.145, No.6, Dec. 1986, 8 pgs.

McDonald MD, et al., "The Regenstrief Medical Record: 1991 A Campus–wide System," AMIA, Inc., 1992, 925–928.

Ogura et al., "On–line prescription order and prescription support in an integrated hospital information system," *Medical Informatics*, vol.10, No.4, Oct./Dec. 1985, 14 pgs.

Picart et al., "A program for parenteral and combined parenteral and enteral nutrition of neonates and children and children in an intensive care unit," *Intensive Care Medicine*, 1989, 4 pgs.

Tierney MD, et al., "Physician Inpatient Order Writing on Microcomputer Workstations," *The Journal of the American medical Association*, vol. 269, No. 3, Jan. 20, 1993, 6 pgs.

Tierney MD, et al., "The Effect on Test Ordering of Informing Physicians of the Charges for Outpatient Diagnostic Tests," *The New England Journal of Medicine*, vol.322, No. 20, May 17, 1990, 7 pgs.

Schroeder et al., "Direct order entry by physicians in a computerized hospital information system," *American Journal of Hospital Pharmacy*, vol.43, Feb. 1996, 6 pgs.

Sittig PhD, et al., "Computer–based Physician Ordr Entry: The State of the Art," *The Journal of the American Medical Informatics Association*, vol.1, No.2, Mar./Apr. 1994, 16 pgs.

Spackman MD, et al., "The Transfusion Advisor: A Knowledge–based System for the Blood Bank," SCAMC, Inc., 1988, 4 pgs.

Sittig PhD, et al., "Implementation of a Computerized Patient Advice System Using the HELP Clinical Information System," *Computers and Biomedical Research*, vol.22, No.5, Oct. 1989, 15 pgs.

Sittig, D.F., and Stead, W.W., 1994, "Computer–based Physician Order Entry: The State of the Art," *J. Am Med. Informatics Assoc.* 1:108–123.

"Mycin", in Barr et al., The Handbook of Artificial Intelligence, vol.II, *Addison–Wesley Publishing Co. Inc.*, ©1982, pp.184–192.

"Digitalis Therapy Advisor," id, pp. 206–211.

* cited by examiner

FIG. 2

| Dosage | Pharmacology | Side Effects | Cost | $Comparison |
|---|---|---|---|---|
| Interactions | Allergies | Pregnancy | Location | Warning |

Index: | albuterol

Patient Information
Name: Krane, Kevin H                                    ID: |19099|         Age: 28
Sex:      |Height:              |Actual Wt:              |Ideal Wt:         LiverDisease
 Male     | FT: 5    In: |9     | Kg: |50                | Kg: |70          Yes
 Female   | Total In Cm: |      | Lb: |110               | Lb: |154         No
Dialysis:                                     Renal Function
 None    Hemo    Peritoneal                    SCr: 1.4 mg/dl    CrCl: |77 ml/min:

CONCOMITANT DRUGS                                Drug Allergies zidovudine

Patient Conditions                      Other
 Condition                              Acute
 Therapy                                Immediate Release Oral
 Dose Form Pharmacy Notes

FIG. 4

| DOSAGE | PHARMACOLOGY | SIDE EFFECTS | $COMPARISON |
|---|---|---|---|
| INTERACTIONS | ALLERGIES | PREGNANCY | LACTATION | WARNING |

SELECT ALL UNDER MENU SELECTION REFERENCES TO SEE DRUG INTERACTION REFERENCES

CEFTAZIDIME: DRUG INTERACTIONS

CEFTAZIDIME & GENTAMICIN:
NEPHROTOXICITY MAY BE POTENTIATED BY COADMINISTRATION OF SOME CEPHALOSPORINS AND GETAMICIN.

PHARMACY NOTES:

| MediSource | | | | | |
|---|---|---|---|---|---|
| DOSAGE | PHARMACOLOGY | SIDE EFFECTS | COST | $COMPARISON | |
| INTERACTIONS | ALLERGIES | PREGNANCY | LACTATION | WARNING | |

CEFTAZIDIME: DOSAGE RECOMMENDATIONS

DOSAGE RECOMMENDATION:

THE DOSE OF CEFTAZIDIME RECOMMENDED FOR THIS PATIENT WITH PYELONEPHRITIS IS 1–2 GRAM(S) INTRAVENOUSLY EVERY 8 HOURS. IF NECESSARY, THIS DOSE MAY BE ADMINISTERED INTRAMUSCULARLY.

ONCE THE PATIENT IS STABLE AND ABLE TO TOLERATE ORAL MEDICATION, ORAL ANTIBIOTICS MAY BE SUBSTITUTED ACCORDING TO MICROBIOLOGY SENSITIVITY DATA.

THERAPY SHOULD BE CONTINUED FOR ABOUT 14 DAYS, DEPENDING ON THE NATURE AND SEVERITY OF THE INFECTION.

THE END.

PHARMACY NOTES:

| DOSAGE | PHARMACOLOGY | SIDE EFFECTS | COST | $COMPARISON |
|---|---|---|---|---|
| INTERACTIONS | ALLERGIES | PREGNANCY | LACTATION | WARNING |

SELECT ALL UNDER MENU SELECTION REFERENCES TO SEE PARMACOLOGY REFERENCES.

CEFTAZIDIME: PHARMACOLOGY AND PARMACOKINETICS

PHARMACOLOGY:

CEFTAZIDIME IS A THIRD GENERATION CEPHALOSPORIN. THE MECHANISM OF ACTION IS INHIBITION OF BACTERIAL CELL WALL SYNTHESIS.

CEFTAZIDIME IS ACTIVE AGAINST A VARIETY OF GRAM POSITIVE, GRAM NEGATIVE AND ANAEROBIC ORGANISMS, HOWEVER IT IS FREQUENTLY USED ONLY FOR THE TREATMENT OF GRAM NEGATIVE INFECTIONS. THIS DRUG IS COMMONLY USED FOR TREATMENT OF INFECTIONS CAUSED BY PSEUDOMONAS AERUGINOSA. MOST STRAINS OF THIS ORGANISM ARE INHIBITED BY CEFTAZIDIME CONCENTRATIONS OF 0.5 – 1 mg/L. OTHER ORGANISMS AGAINST WHICH CEFTAZIDIME IS ACTIVE INCLUDE HAEMOPHILUS INFLUENZAE, KLEBSIELLA PNEUMONIA, AND ENTEROBACTER.

IT IS USED FOR A VARIETY OF INFECTIONS INCLUDING MENINGITIS, FEBRILE NEUTROPENIA, OSTEOMYELITIS, PNEUMONIA AND PYELONEPHRITIS.

CEFTAZIDIME: PHARMACOLOGY REFERENCES

LAROY J, LEGUY F, BORSA F, ET AL. PHARMACOKINETICS OF CEFTAZIDIME IN NORMAL AND UREMIC SUBJECTS. ANTIMICROB AGENTS CHEMOTHER 1984; 25:638–42.
KEYWORD: CLEARANCE, DOSE, ELIMINATION, HALF LIFE, VOLUME.

WELAGE LS, SCHULTZ RW, SCHENTAG JJ. PHARMACOKINETICS OF CEFTAZIDIME IN PATIENTS WITH RENAL INSUFFICIENCY. ANTIMICROB AGENTS CHEMOTHER 1984; 25:201–4.
KEYWORD: CLEARANCE, DOSE, ELIMINATION, HALF LIFE, VOLUME.

LEEDER JS, SPINO M, ISLES AF, ET AL. CEFTAZIDIME DISPOSITION IN ACUTE AND STABLE CYSTIC FIBROSIS. CLIN PHARMACOL THER 1984; 36:355–62.

| MediSource | | | | | |
|---|---|---|---|---|---|
| DOSAGE | PHARMACOLOGY | SIDE EFFECTS | COST | $COMPARISON | |
| INTERACTIONS | ALLERGIES | PREGNANCY | LACTATION | WARNING | |

SELECT LEVEL ONE TO SEE LEVEL TWO SIDE EFFECTS.

CEFTAZIDIME: SIDE EFFECTS        SIDE EFFECTS LEVEL 2

EOSINOPHILIA WHICH IS USUALLY MILD AND TRANSIENT, IS THE MOST COMMON ADVERSE EFFECT OF CEFTAZIDIME

GASTROINTESTINAL SIDE EFFECTS HAVE BEEN REPORTED, INCLUDING SEVERE, PROLONGED DIARRHEA.

INTRAMUSCULAR INJECTIONS MAY CAUSE TRANSIENT PAIN AT THE INJECTION SITE.

MILD HYPERSENSITIVITY REACTIONS HAVE BEEN REPORTED. CROSS REACTIONS MAY OCCUR IN PENICILLIN- ALLERGIC PATIENTS. RARELY ANAPHYLACTIC REACTIONS HAVE OCCURED.

THE MOST COMMON ADVERSE EFFECT OF CEFTAZIDIME THERAPY IS EOSINOPHILLA, WHICH IS USUALLY MILD AND RETURNS TO NORMAL SHORTLY AFTER DISCONTINUATION OF THERAPY. OTHER TRANSIENT HEMATOLOGIC EFFECTS, SUCH AS THROMBOCYTOPENIA, THROMBACYTHEMIA AND LEUKOPENIA, HAVE BEEN SEEN BUT ARE MUCH LESS COMMON.

THE END.

CEFTAZIDIME: SIDE EFFECTS REFERENCES

SHIMADA K, MATSUDA T, INAMATSU T, URAYAMA K. BLEEDING SECONDARY TO VITAMIN K DEFICIENCY IN PATIENTS RECEIVING PARENTERAL CEPHEM ANTIBIOTICS. J ANTIMICROB CHEMOTHER 1984;14:325–30.

GENTRY LO, ANTIMICROBIAL ACTIVITY, PHAMACOKINETICS, THERAPEUTIC INDICATIONS AND ADVERSE REACTIONS OF CEFTAZIDIME. PHARMACOTHER 1985;5:254–67.

LJUNGBERG B, NILSSON-EHLE I, COMPARATIVE PHARMACOKINETICS OF CEFTAZIDIME IN YOUNG, HEALTHY AND ELDERLY, ACUTELY ILL MALES. EUR J CLIN PHARMACOL 1988;34:179–86.

| DOSAGE | PHARMACOLOGY | SIDE EFFECTS | $COMPARISON |
|---|---|---|---|
| INTERACTIONS | ALLERGIES | PREGNANCY | LACTATION | COST — 280 | WARNING |

— 282

CEFTAZIDIME: COST

THE DAILY COST OF CEFTAZIDIME 2 GRAM(S) I.V. EVERY 8 HOURS AT MEDISOURCE GENERAL HOSPITAL IS $47.88.

THE DAILY COST OF CEFTAZIDIME 1 GRAM(S) I.V. EVERY 8 HOURS AT MEDISOURCE GENERAL HOSPITAL IS $23.94.

THE END.

PHARMACY NOTES:

FIG. 9

MediSource

| DOSAGE | PHARMACOLOGY | SIDE EFFECTS | COST | $COMPARISON |
|---|---|---|---|---|
| | ALLERGIES | | | WARNING |

290

DRUGS FOR PYELONEPHRITIS

| DRUG | DAILY COST | DOSAGE |
|---|---|---|
| GENTAMICIN | $2.76 | 130 mg I.V. EVERY 24 HOURS |
| AMIKACIN | $58.82 | 510 mg I.V. EVERY 24 HOURS |
| AMPICILLIN | $1.68 | 1 GRAM(S) I.V. EVERY 6 HOURS |
| CEFAZOLIN | $3.14 | 1 GRAM(S) I.V. EVERY 12 HOURS |
| CEFAZOLIN | $6.28 | 2 GRAM(S) I.V. EVERY 12 HOURS |
| CEFMETAZOLE | $8.94 | 1.50 GRAM(S) I.V. EVERY 12 HOURS |
| CEFOXITIN | $70.80 | 1 GRAM(S) I.V. EVERY 8 HOURS |
| CEFOXITIN | $70.80 | 2 GRAM(S) I.V. EVERY 8 HOURS |
| CEFTAZIDIME | $15.96 | 1 GRAM(S) I.V. EVERY 12 HOURS |
| CEFTAZIDIME | $31.82 | 2 GRAM(S) I.V. EVERY 12 HOURS |
| CEFTRIAXONE | $36.92 | 1 GRAM(S) I.V. EVERY 12 HOURS |
| CIPROFLOXACIN | $28.82 | 200 mg I.V. EVERY 12 HOURS |
| CIPROFLOXACIN | $57.64 | 400 mg I.V. EVERY 12 HOURS |
| IMIPENEM | $20.34 | 0.25 GRAM(S) I.V. EVERY 8 HOURS |
| OFLOXACIN | $14.00 | 200 mg I.V. EVERY 24 HOURS |
| OFLOXACIN | $14.00 | 400 mg I.V. EVERY 24 HOURS |
| PIPERACILLIN | $18.96 | 2 GRAM(S) I.V. EVERY 6 HOURS |
| PIPERACILLIN | $28.44 | 3 GRAM(S) I.V. EVERY 6 HOURS |

FIG. 10

Conditions

CONDITION
ASTHMA

WHAT FORM OF ALBUTEROL?
OTHER

THERAPY
ACUTE
PROPHYLAXIS

DOSING FORM
NEBULIZED
METERED-DOSE INHALER
ROTACAP
IMMEDIATE RELEASE ORAL
SUSTAINED RELEASE ORAL

CANCEL

FIG. 11

```
┌─────────────────────────────────────────────────────┐
│                  INPATIENT ORDER              ─310  │
│  PATIENT: KRANE, KEVIN H    ID: 19099    AGE: 28    │
│  ROOM:    175 WEST ROOM 10  DATE: NOV 17 1993  TIME: 15:35│
│  PREVIOUS ORDERS                                    │
│  ┌──────┬──────┬──────────────────────────────┐     │
│  │ DATE │ TIME │ PHYSICIAN'S ORDERS       ─312│     │
│  ├──────┼──────┼──────────────────────────────┤     │
│  │10/20/93│10:00│ MEDICATIONS:                │     │
│  │      │      │ TYLENOL 250 mg PO PM PAIN    │     │
│  │      │      │ PENICILLIN 250 mg IV EVERY 8 HRS.│ │
│  │      │      │                              │     │
│  └──────┴──────┴──────────────────────────────┘     │
│  CURRENT ORDER                                ─316  │
│  EXPERT SERVICE DOSED  ☐                            │
│  ┌──────────────────────────────────────────┐       │
│  │ MEDICATIONS                              │       │
│  │ GENTAMICIN 130 mg INTRAVENOUSLY EVERY 8 HOURS│   │
│  │                          ─320            │       │
│  └──────────────────────────────────────────┘       │
│  ☐STAT  ☐FIRST DOSE NOW  ☐MAKE PRN  ☐NO GENERIC     │
│  ┌────────┐  ┌────────┐  ┌────────┐         ─322    │
│  │  ADD...│  │ CHANGE │  │ DELETE │                 │
│  └────────┘  └────────┘  └────────┘                 │
│  ┌────────┐              ┌────────┐                 │
│  │  SEND  │              │ CANCEL │                 │
│  └────────┘              └────────┘                 │
│   ─314        ─318                                  │
└─────────────────────────────────────────────────────┘
```

ACYCLOVIR TREE

| CASE | CONDITION | SUBCONDITION | DOSAGE FORM | DIALYSIS | CrCl | LIVER OX |
|---|---|---|---|---|---|---|
| 1 | HERPES SIMPLEX | MUCOCUTANEOUS | INTRAVENOUS | NONE | >=80. | NO |
| 2 | | IMMUNOCOMPRO- | | | | YES |
| 3 | | MISED HOST | | | 50-79.9. | NO |
| 4 | | | | | | YES |
| 5 | | | | | 25-49.9. | NO |
| 6 | | | | | | YES |
| 7 | | | | | 10-24.9. | NO |
| 8 | | | | | | YES |
| 9 | | | | | <10 | NO |
| 10 | | | | | | YES |
| 11 | | | | HEMODIALYSIS | | NO |
| 12 | | | | | | YES |
| 13 | | | | PERITONEAL | | NO |
| 14 | | | | | | YES |
| 15 | | | ORAL | NONE | >=80. | NO |
| 16 | | | | | | YES |
| 17 | | | | | 50-79.9. | NO |
| 18 | | | | | | YES |
| 19 | | | | | 25-49.9. | NO |
| 20 | | | | | | YES |
| 21 | | | | | 10-24.9. | NO |
| 22 | | | | | | YES |
| 23 | | | | | <10 | NO |
| 24 | | | | | | YES |
| 25 | | | | HEMODIALYSIS | | NO |
| 26 | | | | | | YES |
| 27 | | | | PERITONEAL | | NO |
| 28 | | | | | | YES |
| 29 | | MUCOCUTANEOUS | ORAL | NONE | >=80. | NO |
| 30 | | IMMUNOCOMPE- | | | | YES |
| 31 | | TENT HOST | | | 50-79.9. | NO |
| 32 | | | | | | YES |
| 33 | | | | | 25-49.9 | NO |
| 34 | | | | | | YES |
| 35 | | | | | 10-24.9. | NO |
| 36 | | | | | | YES |
| 37 | | | | | <10 | NO |
| 38 | | | | | | YES |
| 39 | | | | HEMODIALYSIS | | NO |
| 40 | | | | | | YES |
| 41 | | | | PERITONEAL | | NO |
| 42 | | | | | | YES |
| 43 | | PROPHYLAXIS | ORAL | NONE | >=80. | NO |
| 44 | | | | | | YES |
| 45 | | | | | 50-79.9. | NO |
| 46 | | | | | | YES |
| 47 | | | | | 25.49.9 | NO |
| 48 | | | | | | YES |

FIG. 12

ACYCLOVIR TREE

| # | | | | | | |
|---|---|---|---|---|---|---|
| 49 | | | | | 10-24.9. | NO |
| 50 | | | | | | YES |
| 51 | | | | | <10 | NO |
| 52 | | | | | | YES |
| 53 | | | | | HEMODIALYSIS | NO |
| 54 | | | | | | YES |
| 55 | | | | | PERITONEAL | NO |
| 56 | | | | | | YES |
| 57 | HERPES SIMPLEX | | INTRAVENOUS | NONE | >=80. | NO |
| 58 | ENCEPHALITIS | | | | | YES |
| 59 | | | | | 50-79.9. | NO |
| 60 | | | | | | YES |
| 61 | | | | | 25-49.9. | NO |
| 62 | | | | | | YES |
| 63 | | | | | 10-24.9. | NO |
| 64 | | | | | | YES |
| 65 | | | | | <10 | NO |
| 66 | | | | | | YES |
| 67 | | | | | HEMODIALYSIS | NO |
| 68 | | | | | | YES |
| 69 | | | | | PERITONEAL | NO |
| 70 | | | | | | YES |
| 71 | VARICELLA-ZOSTER | | INTRAVENOUS | NONE | >=80. | NO |
| 72 | | | | | | YES |
| 73 | | | | | 50-79.9. | NO |
| 74 | | | | | | YES |
| 75 | | | | | 25-49.9 | NO |
| 76 | | | | | | YES |
| 77 | | | | | 10-24.9. | NO |
| 78 | | | | | | YES |
| 79 | | | | | <10 | NO |
| 80 | | | | | | YES |
| 81 | | | | | HEMODIALYSIS | NO |
| 82 | | | | | | YES |
| 83 | | | | | PERITONEAL | NO |
| 84 | | | | | | YES |
| 85 | | | ORAL | NONE | >=80. | NO |
| 86 | | | | | | YES |
| 87 | | | | | 50-79.9. | NO |
| 88 | | | | | | YES |
| 89 | | | | | 25.49.9. | NO |
| 90 | | | | | | YES |
| 91 | | | | | 10-24.9. | NO |
| 92 | | | | | | YES |
| 93 | | | | | <10 | NO |
| 94 | | | | | | YES |
| 95 | | | | | HEMODIALYSIS | NO |
| 96 | | | | | | YES |
| 97 | | | | | PERITONEAL | NO |

FIG. 13

ACYCLOVIR TREE

| # | | | | | | |
|---|---|---|---|---|---|---|
| 98 | | | | | | YES |
| 99 | OTHER | | INTRAVENOUS | NONE | >=80. | NO |
| 100 | | | | | | YES |
| 101 | | | | | 50-79.9. | NO |
| 102 | | | | | | YES |
| 103 | | | | | 25-49.9. | NO |
| 104 | | | | | | YES |
| 105 | | | | | 10-24.9. | NO |
| 106 | | | | | | YES |
| 107 | | | | | <10 | NO |
| 108 | | | | | | YES |
| 109 | | | | HEMODIALYSIS | | NO |
| 110 | | | | | | YES |
| 111 | | | | PERITONEAL | | NO |
| 112 | | | | | | YES |
| 113 | | | ORAL | NONE | >=80. | NO |
| 114 | | | | | | YES |
| 115 | | | | | 50-79.9. | NO |
| 116 | | | | | | YES |
| 117 | | | | | 25-49.9. | NO |
| 118 | | | | | | YES |
| 119 | | | | | 10-24.9. | NO |
| 120 | | | | | | YES |
| 121 | | | | | <10 | NO |
| 122 | | | | | | YES |
| 123 | | | | HEMODIALYSIS | | NO |
| 124 | | | | | | YES |
| 125 | | | | PERITONEAL | | NO |
| 126 | | | | | | YES |

FIG. 14

ACYCLOVIR- DECISION TREE

ACYCLOVIR IS AVAILABLE FOR PARENTERAL USE, AND AS 200 MG CAPSULES AND 800 mg TABLETS.

<u>TOP LEVEL TEXT</u>

DOSAGE RECOMMENDATION

THE DOSAGE OF ACYCLOVIR RECOMMENDED FOR THIS PATIENT (CONDITION) IS (DOSE) mg (ROUTE) (FREQUENCY). (INTRAVENOUS ADMIN) (SWITCH) (DURATION) (DIALYSIS STATEMENT)

(RENAL FAILURE DOSE)

(SPECIAL STATEMENT)

RESISTANCE TO ACYCLOVIR IS BEING SEEN AMONG ISOLATES OF HERPES SIMPLAX VIRUS AND VARICELLA-ZOSTER VIRUS. THESE ISOLATES WOULD BE EXPECTED TO BE RESISTANT TO GANCICLOVIR AS WELL, BUT MAY BE SUSCEPTIBLE TO VIDARABINE AND FOSCARNET.

PHARMACOLOGY

ACYCLOVIR IS AN ANTIVIRAL AGENT WHICH IS CONVERTED INTRACELLULARLY TO ACTIVE ACYCLOVIR TRIPHOSPHATE. ACYCLOVIR TRIPHOSPHATE INTERFERES WITH VIRAL DNA SYNTHESIS AND INHIBITS VIRAL REPLICATION.

ACYCLOVIR IS USEFUL IN THE TREATMENT OF INFECTIONS DUE TO HERPES SIMPLEX VIRUS AND VARICELLA-ZOSTER VIRUS.

RESISTANCE TO ACYCLOVIR IS BEING SEEN AMONG ISOLATES OF HERPES SIMPLEX VIRUS AND VARICELLA-ZOSTER VIRUS. THESE ISOLATES WOULD BE EXPECTED TO BE RESISTANT TO GANCICLOVIR AS WELL, BUT MAY BE SUSCEPTIBLE TO VIDARABINE AND FOSCARNET.

PHARMACOKINETICS

THE BIOAVAILABILITY OF ACYCLOVIR IS POOR, RANGING FROM 15 TO 30%.

THE PLASMA PROTEIN BINDING OF ACYCLOVIR AVERAGES 15%.

THE VOLUME OF DISTRIBUTION AVERAGES 0.7 L/kg IN PATIENTS WITH NORMAL RENAL AND HEPATIC FUNCTION. (RENAL Vd) (cns PENETRATION)

PLASMA CLEARANCE OF ACYCLOVIR RANGES FROM 3.0 TO 4.7 ml/min/kg IN PATIENTS WITH NORMAL RENAL AND HEPATIC FUNCTION. (RENAL Cl)

FIG. 15

THE ELIMINATION HALF LIFE IN PATIENTS WITH NORMAL RENAL AND HEPATIC FUNCTION RANGES FRO 2 TO 3 HOURS. (RENAL HALF LIFE)

RENAL EXCRETION IS THE MAJOR ROUTE OF ELIMINATION OF ACYCLOVIR WITH 70 TO 80% EXCRETED UNCHANGED VIA GLOMERULAR FILTRATION AND TUBULAR SECRETION.

THE ONLY SIGNIFICANT METABOLITE THAT HAS BEEN ISOLATED IS 9-CARBOXYMETHOXYMETHYLGUANINE WHICH ACCOUNTS FOR 9 TO 14% OF AN ADMINISTERED DOSE AND IS NOT ACTIVE.

(LIVER PKS)

(DIALYSIS PKS)

FILL IN TEXT

* DOSES ARE CALCULATED AS mg/kg AND ROUNDED TO THE NEAREST 25 mg. EG: 10 mg/kg X 73 kg= 730 mg ROUNDED TO 725 mg.

CASE: 71-74

DOSE, 10 TO 12 mg/kg
ROUTE: INTRAVENOUSLY
FREQUENCY: EVERY 8 HOURS

CASE: 75-76

DOSE: 10 TO 12 mg/kg
ROUTE: INTRAVENOUSLY
FREQUENCY: EVERY 12 HOURS

CASE: 77-78.

DOSE: 5 TO 6 mg/kg
ROUTE: INTRAVENOUSLY
PREQUENCY: EVERY 12 HOURS

CASE: 79-84

DOSE: 5 TO 6 mg/kg
ROUTE: INTRAVENOUSLY
FREQUENCY: EVERY 24 HOURS

FIG. 16

CASS: 1-4

DOSE: 5 mg/kg
ROUTE: INTRAVENOUSLY
FREQUENCY: EVERY 8 HOURS

CASE: 5,6.

DOSE: 5 mg/kg
ROUTE: INTRAVENOUSLY
FREQUENCY: EVERY 12 HOURS

CASE: 7,8.

DOSE: 5 mg/kg
ROUTE: INTRAVENOUSLY
FREQUENCY: EVERY 24 HOURS

CASE: 9-14

DOSE: 2.5 mg/kg
ROUTE: INTRAVENOUSLY
FREQUENCY: EVERY 24 HOURS

CASE: 15-18,29-32.

DOSE: 200
ROUTE: ORALLY
FREQUENCY: FIVE TIMES A DAY

CASE: 19-28,33-42.

CASE:200
ROUTE: ORALLY
FREQUENCY: THREE TIMES A DAY

CASE: 85-88

DOSE: 800
ROUTE: ORALLY
FREQUENCY: FIVE TIMES A DAY

CASE: 89-92.

DOSE: 800
ROUTE: ORALLY
FREQUENCY: EVERY 8 HOURS

FIG. 17

CASE: 93-98

DOSE: 800
ROUTE: ORALLY
FREQUENCY: EVERY 12 HOURS

CASE: 113-116.

DOSE: 200 TO 800
ROUTE: ORALLY
FREQUENCY: FIVE TIMES A DAY

CASE: 117-120.

DOSE: 200 TO 800
ROUTE: ORALLY
FREQUENCY: EVERY 8 HOURS

CASE: 121-126.

DOSE: 200 TO 800
ROUTE: ORALLY
FREQUENCY: EVERY 12 HOURS

CASE: 99-102.

DOSE: 5 mg/kg TO 12 mg/kg
ROUTE: INTRAVENOUSLY
FREQUENCY: EVERY 8 HOURS

CASE : 103-104.

DOSE: 5 mg/kg TO 12 mg/kg
ROUTE: INTRAVENOUSLY
FREQUENCY: EVERY 12 HOURS

CASE: 105-106.

DOSE: 2.5 mg/kg TO 6 mg/kg
ROUTE: INTRAVENOUSLY
FREQUENCY: EVERY 12 HOURS

FIG. 18

CASE: 107-112 -

DOSE: 2.5 mg/kg TO 6 mg/kg
ROUTE: INTRAVENOUSLY
FREQUENCY: EVERY 24 HOURS

CASE: 43-46

DOSE: 400 mg
ROUTE: ORALLY
FREQUENCY: TWICE DAILY

CASE: 46-56

DOSE: 400 mg
ROUTE: ORALLY
FREQUENCY: ONCE DAILY

CASE: 57-60

DOSE: 12 mg/kg
ROUTE: INTRAVENOUSLY
FREQUENCY: EVERY 8 HOURS

CASE: 61 -62

DOSE: 12 mg/kg
ROUTE: INTRAVENOUSLY
FREQUENCY: EVERY 12 HOURS

CASE: 63-64

DOSE: 6 mg/kg
ROUTE: INTRAVENOUSLY
FREQUENCV: EVERY 12 HOURS

CASE: 65-70

DOSE: 6 mg/kg
ROUTE: INTRAVENOUSLY
FREQUENCY: EVERY 24 HOURS

FIG. 19

CASE: 1.2.57.58.71.72.99.100.

INTRAVENOUS ADMIN: ACYCLOVIR SHOULD BE ADMINISTERED OVER ONE HOUR AND THE PATIENT SHOULD BE ADEQUATELY HYDRATED TO PREVENT CRYSTALLIZATION OF ACYCLOVIR IN THE RENAL TUBULES.

CASE: 3-14.59-70.73-84.101-112.

INTRAVENOUS ADMIN: ACYCLOVIR SHOULD BE ADMINISTERED OVER ONE HOUR AND THE PATIENT SHOULD BE ADEQUATELY HYDRATED TO PREVENT CRYSTALLIZATION OF ACYCLOVIR IN THE RENAL TUBULES. THIS IS ESPECIALLY IMPORTED IN THIS PATIENT WITH DECREASED RENAL FUNCTION.

CASE: 1-42

CONDITION: WITH A HERPES SIMPLEX INFECTION
DURATION: THERAPY SHOULD BE CONTINUED FOR ABOUT 10 DAYS DEPENDING ON THE NATURE AND SEVERITY OF THE INFECTION.

CASE: 43-56

CONDITION: REQUIRING PROPHYLAXIS AGAINST HERPES SIMPLEX INFECTION

CASE: 57-70

CONDITION: WITH HERPES SIMPLEX ENCEPHALITIS
DURATION: THERAPY SHOULD BE CONTINUED FOR ABOUT 10 DAYS OR LONGER DEPENDING ON THE NATURE AND SEVERITY OF THE INFECTION.
CNS PENETRATION: RATS TREATED WITH ACYCLOVIR, 25 mg/kg GIVEN SUBCUTANEOUSLY, DEMONSTRATED PEAK BRAIN TISSUE CONCENTRATION AT 20 MINUTES TO ONE HOUR WHICH WERE 30% OF CONCURRENT BLOOD CONCENTRATIONS.

CASE: 71-84.

CONDITION: WITH A VARICELLA- ZOSTER INFECTION
DURATION: THERAPY SHOULD BE CONTINUED FOR ABOUT 7 TO 10 DAYS DEPENDING ON THE NATURE AND SEVERITY OF THE INFECTION.

CASE : 99-126

CONDITION: WITH A VIRAL INFECTION
DURATION: THERAPY SHOULD BE CONTINUED FOR ABOUT 10, DEPENDING ON THE NATURE AND SEVERITY OF THE INFECTION.

FIG. 20

CASE: 5-14,19-28, 33-42, 47-56, 61-70, 75-84, 89-98, 103-112, 117-126

RENAL FAILURE DOSE: BECAUSE ACYCLOVIR UNDERGOES RENAL ELIMINATION, THE NORMALLY RECOMMENDED DOSE HAS BEEN ADJUSTED FOR THIS PATIENT'S RENAL DYSFUNCTION.

CASE: ALL EVENS

LIVER pks: THERE ARE NO DATA ON THE PHARMACOKINETIC DISPOSITION OF ACYCLOVIR IN PATIENTS WITH LIVER DISEASE, HOWEVER, LITTLE ALTERACTION WOULD BE EXPECTED.

CASE: ALL EXCEPT 1,2,15,16,29,30,43,44,57-58,71,72,85,86,99,100,113,114

RENAL vd: A SLIGHT BUT SIGNIFICANT DECREASE EXISTS FOR PATIENTS WITH RENAL IMPAIRMENT AVERAGING 0.59 L/kg (ASSUMING 70 kg BODY WEIGHT).

RENAL Cl: IN PATIENTS WITH END STAGE RENAL DISEASE THE PLASMA CLEARANCE DECREASES TO APPROXIMATELY 0.4 ml/min/kg.

RENAL HALF LIFE: IN PATIENTS WITH END STAGE RENAL DISEASE THIS INCREASES TO APPROXIMATELY 20 HOURS.

CASE. 11,12,25,26,39,40,53,54,67,68,81,82,95,96,109,110,123,124

DIALYSIS pks: ACYCLOVIR PLASMA CONCENTRATIONS ARE REDUCED APPROXIMATELY 60% FOLLOWING 6 HOURS OF HEMODIALYSIS. DIALYSIS CLEARANCE MEASURED 82 ml/min AND THE HALF LIFE DECREASED FROM 20 HOURS OFF DIALYSIS TO APPROXIMATELY 6 HOURS WHILE ON DIALYSIS.

DIALYSIS STATEMENT ACYCLOVIR IS DIALYZED BY HEMODIALYSIS. DOSES SHOULD BE SCHEDULED TO FOLLOW DIALYSIS SESSIONS OR SUPPLEMENTAL DOSES EQUIVALENT TO THE MAINTENANCE DOSE SHOULD BE GIVEN.

CASE: 13,14,27,28,41,42,55,56,69,70,83,84,97,98,111,112,125,126

DIALYSIS pks: IN PATIENTS MANAGED WITH CONTINUOUS AMBULATORY PERITONEAL DIALYSIS (CAPD), THE DIALYSIS CLEARANCE RANGES FROM 3.6 TO 4.4 ml/min WITH 10 TO 12% OF A DOSE RECOVERED IN THE DIALYSATE OVER 24 HOURS.

FIG. 21

CASE: 1-14,57-70,71-84,99-112

SWITCH: ONCE THE PATIENT IS STABLE AND ABLE TO TOLERATE ORAL MEDICATIONS ORAL THERAPY MAY BE SUBSTITUTED TO COMPLETE THERAPY.

SPECIAL STATEMENT:

CASE: 57-70
ACYCLOVIR IS MORE EFFECTIVE AND LESS TOXIC THAN VIDARABINE FOR HERPES SIMPLEX VIRUS ENCEPHALITIS.

CASE: 29-42

FOR GENITAL HERPES SIMPLEX VIRUS INFECTIONS, ACYCLOVIR IS EFFECTIVE IN TREATMENT OF PRIMARY INFECTION TO REDUCE DURATION OF PAIN, NEW LESION FORMATION, AND VIRAL SHEDDING, THERE IS ONLY MODEST BENEFIT IN THE TREATMENT OF RECURRENT HERPES SIMPLEX EPISODES WITH SHORTENING OF LESION DURATION BY ONLY 24 TO 48 HOURS.

CASE: 43-56

PROPHYLACTIC TREATMENT WITH ACVCLOVIR IS USEFUL IN IMMUNOCOMPROMISED PATIENTS AND PATIENTS WITH FREQUENT AND SEVERE REOCCURANCES.

CASE: 71-98

VARACELLA-ZOSTER INFECTIONS ARE MORE SERIOUS IN IMMUNOCOMPROMISED HOSTS. FOR PRIMARY VARICELLA-ZOSTER INFECTIONS IN IMMUNOCOMPROMISED HOSTS, TREATMENT WITH INTRAVENOUS ACYCLOVIR REDUCES THE INCIDENCE OF VARICELLA-ZOSTER VIRUS PNEUMONIA. FOR REACTIVATION OF VARICELLA-ZOSTER VIRUS IN IMMUNOCOMPROMISED PATIENTS, ACYCLOVIR DECREASES THE INCIDENCE OF SEVERE PROGRESSION OF DISEASE (VISCERAL OR SEVERE CUTANEOUS DISSEMINATION) WHEN GIVEN INTRAVENOUSLY. IN NORMAL SUBJECTS ORAL ACVCLOVIR DECREASES THE INCIDENCE OF EARLY PAIN BUT NOT THE INCIDENCE OF SEVERE POSTHERPETIC NEURALGIA, AND REDUCES DURATION OF THE RASH. OPHTHALMIC VARICELLA-ZOSTER WARRANTS TREATMENT WITH ACYCLOVIR GIVEN THE ASSOCIATED MORBIDITY.

FIG. 22

PROVIDING PATIENT-SPECIFIC DRUG INFORMATION

This application Ser. No. 09/189,731 is continuation of Ser. No. 08/629,763 Apr. 9, 1996 U.S. Pat No. 5,833,599 which is a continuation of Ser. No. 08/167,286 Dec. 13, 1993 abandoned.

BACKGROUND

The present invention relates to systems and methods for providing patient-specific drug information.

The effective and safe administration of pharmaceuticals to patients has become more challenging because of two developments. One is the ever increasing population of patients, as medical treatment becomes more sophisticated, and the other is the growing number of drugs available for the treatment of disease, with an ever increasing amount of information about these drugs becoming available.

Over the past 30 years, the number of FDA approved prescription drug products has increased from 650 to 9,500 drugs. In addition, over 100,000 articles relating to drug therapy are published each year. Major advances in analytical methodology have allowed for the specific and sensitive measurement of drugs and their metabolites in biological fluids. This has permitted the definition of mathematical parameters for describing drug metabolism and disposition in the body. The study of pharmacokinetics (what the body does to drugs) has grown in sophistication so that knowledge of elimination and distribution parameters has allowed for specific dosage regimens to be developed in patients based upon the degree of organ function. This permits proper doses of therapeutic agents to be calculated.

The two primary ways in which drugs are eliminated from the body are by the kidney and the liver. These organs serve to detoxify and excrete drugs from the body, and when their function is diminished, accumulation of drugs or drug metabolites may occur. Progressive reduction in renal or liver function by disease or simply by the aging process have been associated with changes in the disposition of many drugs. Alterations have been demonstrated in absorption, protein binding, distribution, elimination, and metabolism.

These considerations affect the growing number of patients with organ dysfunction who receive medication. Renal failure patients on dialysis as well as thirty percent of elderly patients receive an average of eight prescription medications daily. In addition, patients with end-stage organ failure undergoing organ transplantation receive numerous medications aimed at modulating the immune system and fighting infection.

Thus, there is a need for systems and methods capable of providing the clinician with ready and convenient access to current, pertinent, and patient-specific drug information and dosing recommendations.

SUMMARY

In general, in one aspect, the invention features a system for processing data relating to use of an index drug by a patient, by which the identity of the index drug and information about the patient are received and a dosage of the index drug is determined on the basis of the information about the patient. Embodiments of the invention include the following features. A cost for the dosage of the index drug is determined. Pharmacology and pharmacokinetics for the index drug are reported. An alternative drug to the index drug, and a dosage for the alternative drug, are determined on the basis of the information about the patient. A cost for the dosage of the alternative drug is determined. A prescription for the index drug is prepared. Citations to published references are reported. Designation of a set of drugs is received and possible drug interactions are reported. The mechanism and clinical management of the possible drug interactions are reported. A designation of administered drugs and of drug allergies is received and possible allergic reactions are reported. Drug side effects and contraindications and warnings are reported.

In general, in another aspect of the invention, the identity of the index drug and information about the patient are received and information relating to use of the index drug is adapted on the basis of the information about the patient and reported. Further embodiments of the invention include the following features. Information on use of the index drug during pregnancy, information on use of the index drug during lactation, and information about drug administration is reported. Citations to published references relating to other reported information are reported. Indication is given when possible allergic reactions, possible drug interactions, warnings, contraindications, or pertinent pregnancy or lactation information are present. In general, in another aspect, the invention features a user interface method for enabling a user to interact with a computer with respect to information relating to use of an index drug by a patient, which includes enabling the user to designate the index drug, prompting for, and enabling the user to supply information about the patient, and displaying a dosage of the index drug based on the information about the patient. Embodiments of the invention include the following steps. Displaying a set of candidate drugs and enabling the user to select one of them as the index drug. Displaying a set of drug categories, enabling the user to select one, and displaying as candidate drugs those drugs belonging to the selected category. Displaying subcategories of the selected category, enabling the user to select one of the subcategories, and displaying as candidate drugs those drugs belonging to the selected subcategory. Further embodiments of the invention include the following features. Enabling the user to designate a clinical condition for which the index drug would be used and displaying, as an alternative drug to the index drug, a drug for the clinical condition.

In general, in another aspect, the invention features a method for processing data relating to use of an index drug by a patient, which includes receiving the identity of the index drug and information about the patient and determining a dosage of the index drug on the basis of the information about the patient. Further embodiments of the invention include the following features. Receiving information about the patient selected from the patient's age, height, weight, sex, kidney function, liver function, and the clinical condition for which the index drug would be used. Searching data files for records pertaining to the index drug and building a message with information derived from the records.

In general, in another aspect, the invention features a system for processing data relating to use of an index drug selected from a set of drugs having a computer coupled to direct access storage on which are stored data files including a dosage data file, a cost data file, and a drug information file with text relating to a drug in the set, and instructions programming the computer to report text from drug information files pertinent to selected drugs. Further embodiments include the following features. A knowledge base for each drug is provided and the system has instructions to invoke drug knowledge bases. The drug information files include pharmacology information files (including pharmacology and pharmacokinetics), pregnancy, lactation, warnings and contraindications, and side effects information files. Each drug in the set of drugs has a separate knowledge base, a separate dosage data file, a separate cost data file, and a separate group of drug information files. Instructions assemble text pertinent to a selected drug from a drug information file, search for variables in the assembled text, obtain fill-in text to replace the variables, and report the resulting text. Instructions report text from an interactions information file that is pertinent to a selection of drugs, the interactions file having text descriptive of possible drug interactions. An allergy class file defines as allergy classes sets of drug categories; a drug category file defines drug categories for each drug in the set of drugs; and instructions form a patient collection of drugs and an allergies collection of drugs and categories, match the patient collection against the allergies collection for indications of allergic cross-reactivity, and report indicated allergic cross-reactivity.

In general, in another aspect, the invention features a system for processing data relating to use of an index drug, where the system has digital information about a set of drugs, a computer interface for receiving the identity of the index drug and information about the patient, and a subsystem for determining a dosage of the index drug on the basis of the information about the patient. Further embodiments of the invention has the following features. A subsystem calculates a cost for the dosage. Subsystems determine an alternative drug, a dosage for the alternative drug, and a cost for the dosage of the alternative drug.

Computer interfaces receive the identities of concomitant drugs and of drug allergies, and subsystems report possible drug interactions on the basis of the index and concomitant drugs, possible allergic reactions on the basis of the index and concomitant drugs and the drug allergies, and warnings and contraindications to use of the index drug.

Among the advantages of the invention are the following:

Using the systems and methods of the invention one can provide ready access to current, patient-specific drug information and dosing recommendations for a clinician in a clinical setting. With its patient-specific focus, the invention operates intuitively to provide users with the information of interest to them. The invention allows the presentation, through one interface, of information about the dosages, costs, pharmacology, pharmacokinetics, interactions, allergic reactivity, side effects, warnings, contraindications, and effects during pregnancy and lactation of any number of drugs. The user may also obtain publication references tied to and supporting the drug information, thereby increasing user confidence in the information received.

Systems of the invention are configurable so that a vendor or customer may readily update the substantive information provided to the user and, in addition, a customer may readily provide its own information. As illustrated by the described embodiment, systems of the invention are readily portable to a variety of hardware and software platforms, including personal computers, work stations, minicomputers and mainframe computer platforms, in stand-alone and network configurations. This flexibility allows the systems and methods of the invention to be run on, or in conjunction with, customer platforms and systems supporting, for example, hospital information systems or clinical patient data bases, thereby facilitating exchange and integration of information.

Other advantages and features will become apparent from the following description and from the claims.

BRIEF DESCRIPTION OF THE DRAWINGS

FIG. 2 illustrates the main user interface window.

FIG. 4 illustrates the display of drug interactions information.

FIG. 5 illustrates the Dosage Recommendations window.

FIG. 6 illustrates a window displaying pharmacology information, showing supporting references.

FIG. 7 illustrates the Side Effects window, showing level one and level two information.

FIG. 8 illustrates the display of cost information for the index drug.

FIG. 9 illustrates the display of cost comparison information for alternatives to the index drug.

FIG. 10 illustrates a window requesting patient information.

FIG. 11 illustrates a window used to prepare prescriptions or orders.

FIGS. 12–22 shows an illustrative decision tree, for the drug acyclovir.

DESCRIPTION

Figure 1:
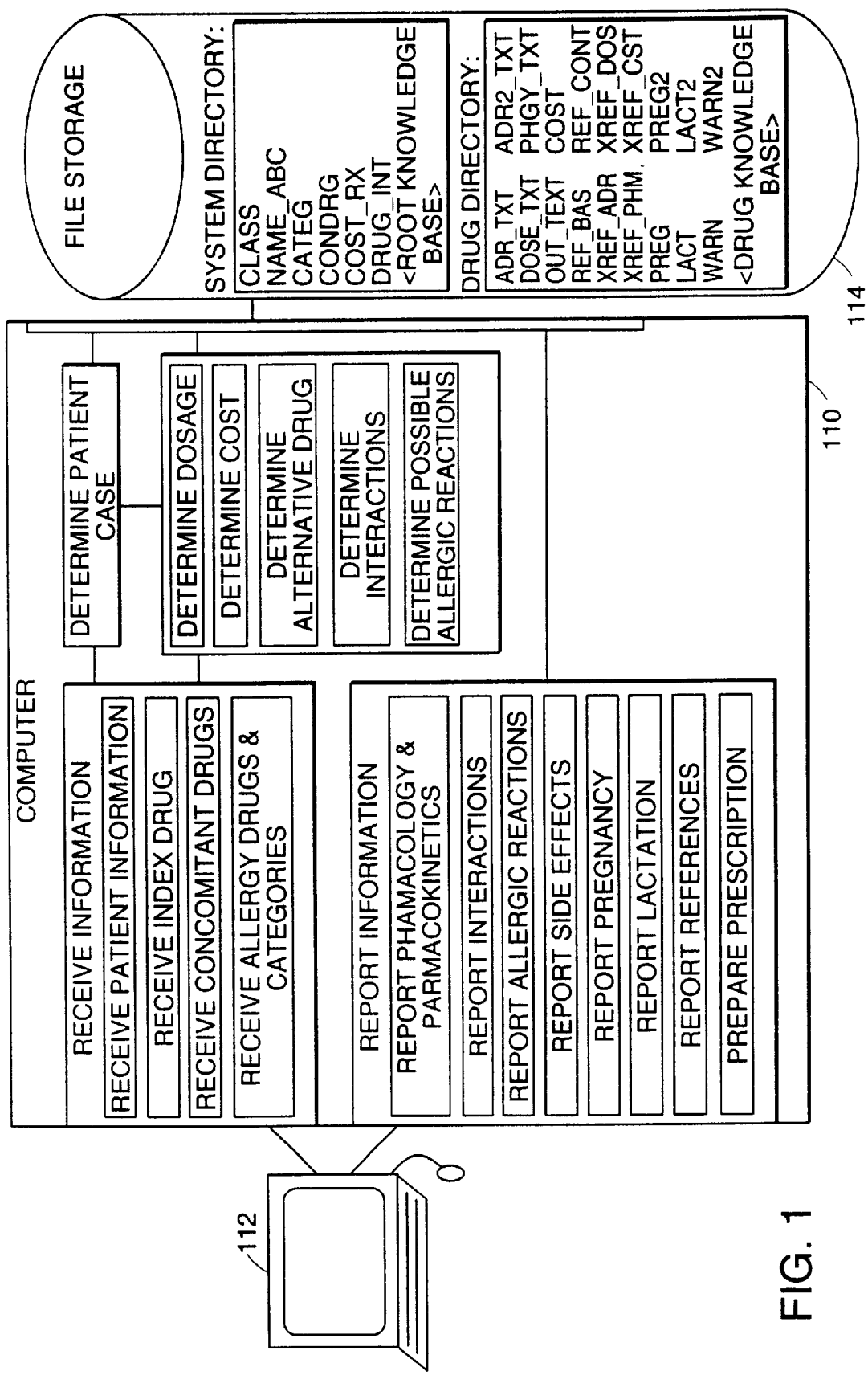
FIG. 1 is a block diagram of the components of an embodiment of the system.

Turning to FIG. 1, a system for processing data relating to use of drugs by a patient is implemented in a general purpose computing platform having a computer 110, an interactive user interface device 112, and direct access storage 114. The system preferably has a graphical user interface, by which the user obtains information and directions from windows shown on a display monitor and provides information to the system, and direct the operation of the system, using a keyboard and pointing device such as mouse. The system also has a printer (not shown) to print prescriptions, drug orders, citations to references, and all other information generated by the system.

Using the system, the user identifies the "index drug" (the drug in reference to which the system operates); enters and edits patient information, displays and prints information on recommended dosage, pharmacology, lactation, pregnancy, warnings, contraindications, side effects, drug interactions, allergic reactivity, and references, all relating to the index drug and, as appropriate, concomitant drugs (i.e., any other drugs the patient is taking). Using the system, the user also displays, edits, and prints prescriptions and drug orders. (The index drug and the concomitant drugs may for convenience be referred to collectively as the "administered drugs". This does not mean that the system requires the index drug be administered: the user may use the system simply to learn about a drug.)

The system indicates to the user when information that may be of interest is available. For example, the system indicates that information is available concerning interactions that may arise from concomitant use of the administered drugs, and makes more information on the interaction (s) available to the user. The system provides comparable functionality for drug allergies. Similarly, if the patient is a female of child-bearing age, the system indicates that information concerning pregnancy and lactation is available, to remind the user to review the information.

When the system needs further information to perform a function, the system prompts the user for the information. The user may change information at any time and thereby see how the changes affect the dosage recommendations and other patient-specific information provided by the system.

When the system displays information, patient-specific portions of the displayed information are highlighted. When information is available at multiple levels of detail or generality, the user may step the display from one level to another. The system displays references that support displayed information.

As part of its internal processing, the system determines the patient "case". Specific to each drug, the case is a number that uniquely represents a set of clinical factors relevant to dosing the drug. The system determines the patient case for a drug by running a knowledge base specific to the drug in an expert system shell.

The system is implemented in two parts: one part is a program written in the language C, which controls the system's user interface and data files. The other part is a set of drug-specific knowledge bases and an expert system shell, Nexpert Object, which is invoked by the C program. (Nexpert Object is a trademark of, and the software is available from, Neuron Data, Inc. of Palo Alto, Calif.)

The system may be used by one or more users. The system will normally be installed in a hospital or other clinical setting, which will be referred to as the customer, and the customer may connect the system to other data processing systems to exchange information, such as information about patients, drug availability, and costs, or to place drug orders.

The Main Window. Turning to FIG. 2, the main user interface window 200 is shown. This presents a graphical user interface of the conventional kind. The interface illustrated was created using Neuron Data's Open Interface and is displayed using OSF/Motif. (Open Interface is a trademark of, and the software is available from, Neuron Data, Inc. of Palo Alto, Calif.; OSF and Motif are trademarks of Open Software Foundation, Inc.)

The main window presents a menu bar 202 with the following top-level menus: Patient, Drug, Condition, References, Orders, Print and Help.

In the main window below the menu bar are the function buttons 204 for the major features of the system: Dosage, Pharmacology, Side Effects, Cost, $Comparison, Interactions, Allergies, Pregnancy, Lactation, and Warning. Certain of these buttons are highlighted, when appropriate, to alert the user to available information.

In the main window below the function buttons is a status bar 206, which will contain instructions to the user about entering data and obtaining information from the system.

In the main window below the status bar are three main areas: the patient information area 208, the patient conditions area 210, and the pharmacy notes area 212. The patient information area 208 records demographic and clinical information about the patient. The patient conditions area 210 lists choices and diagnoses entered by the user. The pharmacy notes area displays any customer messages concerning the index drug to system users.

Figure 3:
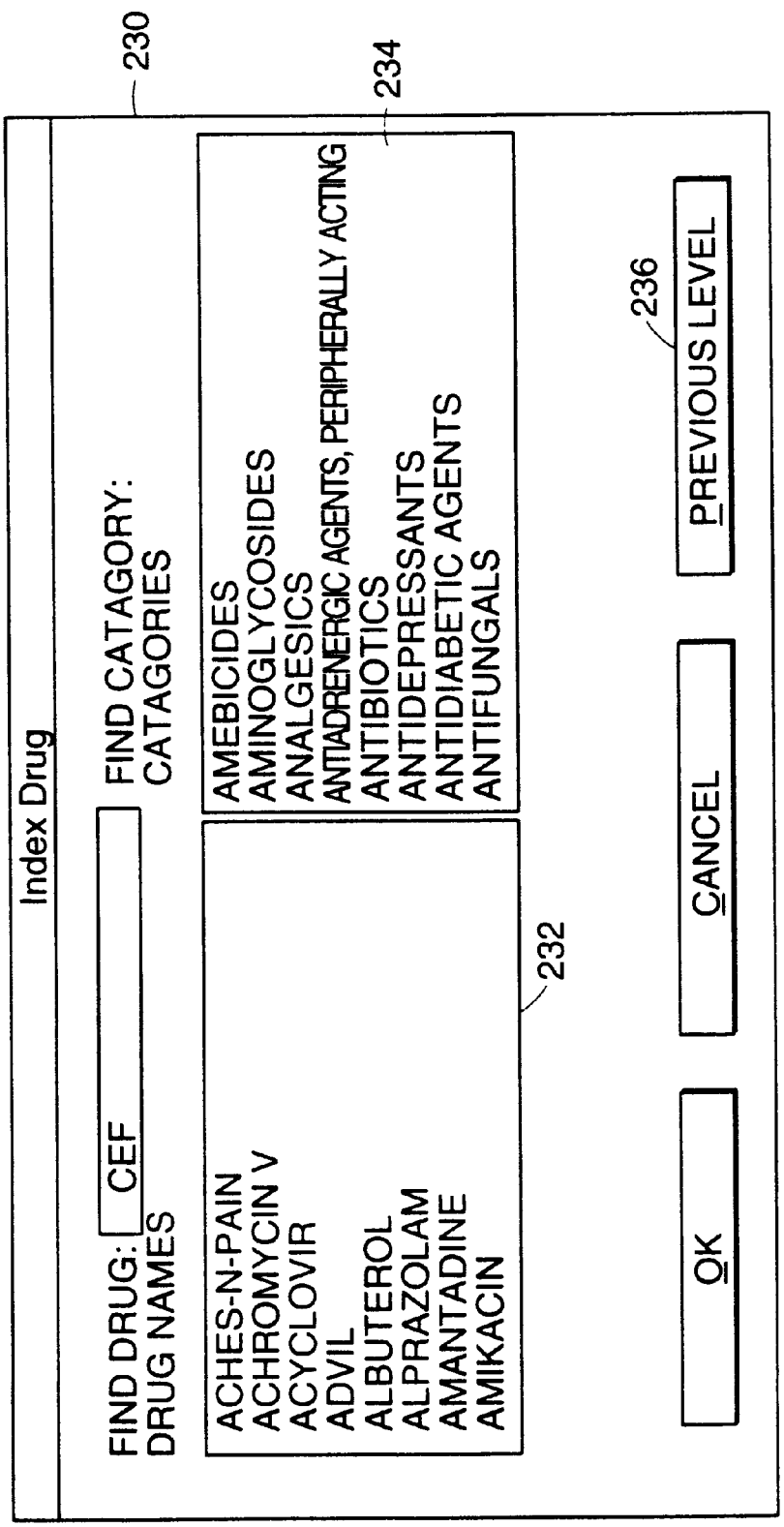
FIG. 3 illustrates the Choose A Drug window.

The Index Drug. As the first step in using the system, the user may select the drug (the "index drug") on which the user wishes information. The user can do so by entering a drug name in the Index Drug field of the main window or the user can obtain from the Drug menu the Choose A Drug window 230, illustrated in FIG. 3. In the Choose A Drug window, the system displays two lists: (1) a list of drugs 232, on the left-hand side, and (2) a list of therapeutic categories 234, on the right-hand side. Drugs are listed by both trade and generic name. If the user has selected a category, the drugs displayed in the left-hand list are only those drugs in the selected category (including all depths of subcategories) and the right-hand category list then contains only the subcategories of the selected category, which the user may then select from, as long as there are subcategories to select.

By selecting the Previous Level button 236, the user may return to the previous category or subcategory. Thus, the user may navigate the category tree to find the desired drug.

Patient Information. The patient information area 208 of the main window is used to enter and change patient data (which occasionally is referred to herein as the patient profile), including patient name, patient identification, sex, height, actual weight, ideal weight, dialysis status, serum creatinine, creatinine clearance, concomitant drugs, liver disease status, and known drug allergies. The system allows the user to enter and change information in any order.

The system has a default patient, John Q. Public, a 35 year old, 5 foot 9 inch, 70 kilogram male with a serum creatinine of 0.9 mg./dl., with no liver disease and no known drug allergies or concomitant drugs. If the user selects patient John Q. Public, the system sets all patient data to the default values. Unless the patient is John Q. Public, the system will not use default values for any patient data fields. Thus, before running a knowledge base (to calculate drug doses or costs, which will be described later), the system confirms that the user has entered values for patient age, weight, height, sex, liver disease, dialysis status, and, if the patient is not on dialysis, serum creatinine. If any values have not been entered, the system requests the user either to provide the missing information or to select the default patient, John Q. Public.

If the system is coupled to computer-accessible hospital or clinic records (for example, by a communications link to a hospital information system or by access to a hospital database), the system may automatically acquire information based on the patient's name or the patient's hospital or clinic ID number.

When the user enters an age for the patient, the systems performs the following steps. If the age entered is out of the range 18–100, the system asks the user to reconfirm the age. If the value is not confirmed, the system ignores the entry. (The system described does not provide pediatric information, so it will not accept an age less than 18.) If the patient is a female of less than 50 years, the systems highlights the Lactation button and gets a pregnancy category for the index drug, puts the category letter into the Pregnancy button and highlights the Pregnancy button. If the ideal weight and the serum creatinine are known, the system calculates and displays the creatinine clearance. Finally, if the index drug's knowledge base has been run for the current patient, the case number is set to zero (a non-existing case). This allows index drug information to be displayed without patient-specific content, and indicates that the knowledge base needs to be rerun when dosage or cost information is requested.

When the user enters a sex for the patient, the system performs the following steps. If the sex entered is female and the age is less than 50, the system highlights the Lactation and Pregnancy buttons as described above. If the sex entered is not female, the Lactation and Pregnancy buttons' highlighting, if any, is cleared. If the height is known, the system calculates and displays ideal weight. If the age, ideal weight and serum creatinine are known, the system calculates and displays creatinine clearance. Finally, if the index drug's knowledge base has been run for the current patient, the case number is set to zero.

When the user enters a height for the patient, the system performs the following steps. If the height entered is out of the range 4 feet to 7 feet, the system asks the user to reconfirm the height. If the value is not confirmed, the system ignores the entry. If the sex is known, the system calculates ideal weight in kilograms by the formula ideal weight=45 (for females) or 50 (for males) ±2.3×(inches in height above/below 5 feet).

Then, if age and serum creatinine are known, the system calculates and displays creatinine clearance. Finally, if the index drug's knowledge base has been run for the current patient, the case number is set to zero.

When the user enters an actual weight for the patient, the system performs the following steps. If the actual weight is out of the range of 80–275 pounds, the system asks the user to reconfirm the weight. If the value is not confirmed, the system ignores the entry. The weight is displayed in both pounds and kilograms (the system calculating the units not entered). Finally, if the index drug's knowledge base has been run for the current patient, the case number is set to zero.

Although the system will calculate a value for the patient's ideal weight, the user may override the calculated value. When the user enters a value in the ideal weight field, the system performs the following steps. If the ideal weight entered is out of the range of 80–275 pounds, the system asks the user to reconfirm the weight. If the value is not confirmed, the system ignores the entry. If the age, serum creatinine and sex are known, the system calculates and displays creatinine clearance. Finally, if the index drug's knowledge base has been run for the current patient, the case number is set to zero.

When the user enters a value in the liver disease field, the system, if necessary, sets the case number to zero if the index drug's knowledge base has been run for the current patient.

When the user enters a value in the dialysis field, the system performs the following steps. If the value of dialysis is not "none", the system displays "n/a" (not applicable) in the SCr (serum creatinine) and CrCl (creatinine clearance) fields and disables entry of data into these two fields. (They are meaningless in the context of dialysis.) Finally, if the index drug's knowledge base has been run for the current patient, the case number is set to zero.

When the user enters a value in the serum creatinine field, the system performs the following steps. If the serum creatinine entered is out of the range 0.4–2.0 mg./dl., the system asks the user to reconfirm the value. If the value is not confirmed, the system ignores the entry. If the age, ideal weight, and sex are known, the system calculates and displays creatinine clearance. Finally, if the index drug's knowledge base has been run for the current patient, the case number is set to zero.

The system assumes stable renal function and calculates creatinine clearance according to the Cockcroft-Gault formula using the information in the serum creatinine, age, ideal weight, height, and sex fields. (Donald W. Cockcroft & M. Henry Gault, *Prediction of Creatinine Clearance from Serum Creatinine,* Nephron 16:31–41 (1976).) Nevertheless, the user may enter a value in the CrCl field. If the user does enter a value, it overrides the calculated value, in which case the system sets the case number to zero if the index drug's knowledge base has been run for the current patient.

Concomitant Drugs. The system maintains in volatile memory a set or list of concomitant drugs for the current patient. The user may add drugs to, and delete drugs from, the list of concomitant drugs, which is displayed in the Concomitant Drugs area 214 of the main window 200. Concomitant drugs may also have been obtained from a hospital information system or a database coupled to the system. When the user deletes drugs from the list, the system preliminary clears any highlighting from the Interactions button. After drugs are added to or deleted from the list, the system searches for drug interactions. If the system detects an interaction between any two administered drugs, the system highlights (e.g., colors or darkens) the Interactions button.

To determine if there is an adverse or other type of drug interaction, the system checks each administered drug for an individual interactions warning and all pairs of administered drugs against each other to determine if there is an interaction known to the system. The data file drug_nt.dbf (described in Table 2) has an entry for each drug and pair of drugs known to the system to have an interaction effect, along with an indication of the effect's severity. If there is an entry in drug_int.dbf for any of the administered drugs, the Interaction button is highlighted (for example, with different colors) in a way that indicates the severity of the most severe interaction: mild, moderate or major. The Interactions button also highlights if the system detects a general interactions warning associated with any individual administered drug.

Drug Allergies. Using the Drug Allergies area 216 of the main window, the user may designate to the system the drugs and allergy categories to which the patient is allergic. (As with patient profile information and concomitant drugs, the system may be configured to obtain this information automatically from a hospital information system or other source.)

If allergies are designated (either by the user, as just described, or in patient records obtained electronically from a hospital or clinic information system, or the like), the system checks the administered drugs for allergies or possible cross-category allergies. If any are found, the Allergy button is highlighted. The Allergy button is highlighted when any administered drug is the same as a drug designated as an allergy, is in an allergy category containing a drug designated as an allergy, is in an allergy category designated as an allergy, or is in an allergy category that possibly cross-relates to an allergy category designated as an allergy.

The Patient Condition. Turning to FIG. 4, the system may (in the course of processing a user request) require information about the patient's clinical condition to determine a dosage or cost, or to provide other drug information. If so, the system will ask the user one or more questions. The information required will vary according to the patient and the index drug. As illustrated in FIG. 4, the user may be asked to identify the condition for which the index drug would be used, its severity, and the mode of drug administration. The user may enter and modify information about the patient's condition at any time. When the user does so, the system resets the knowledge base and drug-specific patient data. Preferably, the system will only reset the modified information and that portion of the drug-specific patient data that might have been calculated on the basis of the information that has been modified.

Function buttons. The function buttons 204 include Dosage to request dosage information, Pharmacology to request information on pharmacology and pharmacokinetics, Side Effects to request information about side effects, Cost to request cost information on the index drug, $Comparison to request cost comparison information on the index drug and other drugs used for the patient's condition, Interactions to request information about interactions of administered drugs, Allergies to request information relating to allergic reactions, Pregnancy to request information relating to use of the index drug during pregnancy, Lactation to request information relating to use of the index drug during lactation, and Warning to request any contraindications or other warnings that may exist concerning the index drug.

After the user selects a function button, the system presents a window displaying the desired information. All patient-specific portions of the displayed information are highlighted (for example, with color or italics) so that users can immediately identify the patient-specific fill-in text. Depending on the function, further information may be available by scrolling the window or by selecting an entry in a left-hand window to cause more details to be displayed in the companion right-hand window. The system makes citations to reference sources used to generate the information displayed available to the user through the References menu.

Dosage. Turning to FIG. 5, the user selects the Dosage function button 250 to display drug dosage information. In response, the system displays in the Dosage Recommendations window 252 a dosage recommendation and related information that takes into account the patient's profile and clinical condition. At the user's request, the system will display citations to references for the dosage information.

The dosage information may indicate that the dosage has been adjusted to take into account the patient's renal or liver function. The dosage information may contain instructions on monitoring the patient for the duration of the drug administration. The dosage recommendation may be for a simple dose, a range of doses, or a set of doses or ranges of doses (such as an initial dose and a maintenance dose), each having associated with it a form of administration.

When the user selects Dosage, the system performs the following steps. The system assembles the top-level text from the data file dose_txt.dbf (described in Table 1). If there are no variables in the text, the text is simply displayed. Otherwise, the index drug's knowledge base is run to determine the patient case, if the patient case is unknown or if the patient case is known and has a value of zero. Then, information generated by the knowledge base and fill-in text from the data files xref_dos.dbf and out_text.dbf (described in Table 1) are used to replace variables in the top-level text. Any variables in the top-level text for which fill-in text has not been found are deleted. Then, the resulting text is displayed.

Pharmacology. As illustrated in FIG. 6, the user selects the Pharmacology function button 260 to display pharmacologic and pharmacokinetic information on the index drug. In response, the system presents information describing the index drug, how it works, and the situations in which it is used. The system also provides information on the following topics: bioavailability, protein binding, volume of distribution, plasma clearance, half life, metabolism, elimination, and dialysis, where applicable.

When the user selects Pharmacology, the system performs the following steps. The system assembles the top-level text from the data file phgy_txt.dbf (described in Table 1). If there are no variables in the text, it is simply displayed. For some drugs, pharmacologic and pharmacokinetic information may include patient-specific information. For this reason, the system may be configured to determine the patient case (if it is unknown or zero) at this time. Preferably, however, the system is configured simply to provide the information without reference to patient-specific information, so as not to interrupt the user with requests for information. Any information generated by the knowledge base and fill-in text from the data files xref_phm.dbf and out_text.dbf (described in Table 1) are used to replace variables in the top-level text, if the case is known and not zero. Any variables in the top-level text for which fill-in text has not been found are deleted. Then, the resulting text is displayed 262.

To view a list of the references used to generate the pharmacologic and pharmacokinetic information, the user uses the References menus. As illustrated in FIG. 6 at window 264, the system will display citations to references used along with keywords indicating the topic(s) to which they relate.

Side Effects. As illustrated in FIG. 7, the user selects the Side Effects function button 270 to display information on the index drug's side effects. For some drugs, side effects information may include patient-specific information. The system displays side effects in two levels. Level one 272 briefly describes the most serious and most common adverse effects of a drug. Some of these effects have more detailed, level two, information 274 associated with them, typically a case report about the particular level one effect. As illustrated in FIG. 7, the user may select a level one entry 276 to request the system to display its associated level two information, if any.

When the user selects Side Effects, the system performs the following steps. The system assembles the top-level text from the data file adr_txt.dbf (described in Table 1). If there are no variables in the text, the text is simply displayed. For some drugs, side effects information may include patient-specific information. For this reason, the system may be configured to determine the patient case (if it is unknown or zero) at this time. Preferably, however, the system is configured simply to provide side effects information without reference to patient-specific information, so as not to interrupt the user with requests for information. Any information generated by the knowledge base and fill-in text from the data files xref_adr.dbf and out_text.dbf (described in Table 1) are used to replace variables in the top-level text, if the case is known and not zero. Any variables in the top-level text for which fill-in text has not been found are deleted. Then the resulting text is displayed.

Cost. As illustrated in FIG. 8, the user selects the Cost function button 280 to request the system to determine and display the daily cost of the recommended therapy. The cost is a range if the recommended dosage was a range. The system is configurable to present multiple costs if the recommended doses are multiple, as in the case of a loading dose and a maintenance dose. Preferably, however, the system is configured to present the costs of only the maintenance doses, for clarity in the presentation of comparative information to the user. For the same reason, the system is configured to use the unit dose for cost calculations of drugs that are used "as needed".

The system is configurable to use a customer's actual cost information, or as a default, it can use pre-selected average costs. The system is also configurable to include in the cost calculation the costs associated with drug administration.

When the user selects Cost, the system performs the following steps. If the patient case is not known, or if the patient case is zero, the knowledge base for the index drug is first run. Having the index drug and the patient case, the system searches the data file xref_cst.dbf (described in Table 1) for records with a matching case number. For each record found, the system enters the record's fields' values in a list or, if in the record the Use_KB field is set, the values are taken from Calc_Dose objects in the knowledge base. There will be one entry in the list for each dose, because the file xref_cst.dbf has one record for each dose for each case. Thus, for example, if a case calls for a loading dose of 500 to 600 mg./kg. and a maintenance dose of 200 to 500 mg./kg., xref_cst.dbf will have four records for the case and the list will have four entries. (The Calc_Dose objects and the knowledge base are described later.)

For each entry in the list, the system finds each record in the data file cost.dbf (described in Table 1) that has the same Units and the Dosage_form as the list entry, and for each record the system calculates a cost using the formula identified in the Formula field of the record. The lowest cost calculated for all the records for a list entry is the cost reported to the user for that entry's dose. Then, for each dose to be administered, i.e., for each list entry, the system displays 282 the cost, dose, mode of administration, and frequency of administration. Although the system could do so, the system does not calculate the lowest cost that could be achieved by mixing units (for example, tablets) of a different size, because such mixing is contrary to general pharmacy practices.

A number of cost calculation formulas are programmed in the system. The field Formula in cost.dbf identifies the one to be used. Although the system can be configured with cost formulas of any degree of complexity, three simple formulas are generally sufficient for cost and cost comparison purposes. The first cost formula calculates the daily cost by dividing the recommended dose by the available dose size and then rounding up, if necessary, to the next integer (to yield the whole number of dose sizes needed to achieve the recommended dose), which whole number is multiplied by the price per dose size times the number of administrations per day to yield the daily cost. The dose size and the unit prices are found in the file cost.dbf. The second cost formula first calculates the daily recommended dose by multiplying the recommended dose by the frequency of administration, then calculates the whole number of dose sizes needed in a day, then multiplies that number by the price per dose size. The third cost formula sets the daily cost to the unit price, which is appropriate, for example, when the units are indivisible and greater than any patient's requirement.

Cost Comparison. As illustrated in FIG. 9, the user selects the $Comparison function button 290 to request cost comparison information for the patient. The system extracts a set of alternative drugs—for example, all drugs with FDA approval and/or all drugs that are commonly used for treating the patient's condition—from the data file condrg.dbf (described in Table 2) and collects them in a list. The system displays cost-related information for the collected alternative drugs, sorted by cost, with the least expensive therapy displayed first. Alternatively, the system may have the user select one or more drugs for comparison. For each drug the system determines the patient case, recommended dosage, and cost as described above, and displays the drug name, recommended dosage, route of administration, and daily cost of therapy. Because each patient case is drug-specific, the system may request additional information from the user to use in dosing the drugs selected for cost comparison.

Interactions. Turning to FIG. 4, the user selects the Interactions function button to display interactions information. When the user selects Interactions, the system performs the following steps. The system first builds a list of all single administered drugs and of all combinations of two administered drugs. For each entry in the list, single drug or pair, the system looks for a record in the data file drug_int.dbf (described in Table 2). If a record is found, the system displays the corresponding text. When there are no more entries in the list, the system adds either "no other interactions found" or "no interactions were found" text to the display, depending on whether any interactions messages had been displayed.

Allergies. Returning to FIG. 1, the user selects the Allergies function button to display allergy information. When the user selects Allergies, the system performs the following steps. The system builds a list (the "patient drug list") based on all the administered drugs (the index drug and the concomitant drugs, as in window 214). Each element of this list includes Name of the drug, Drug_ID of the drug, Allergy category of the drug (if any), and Name of allergy class of the drug (if any).

(The system's drug category information is stored in data files alrgdr.dbf and alrgnm.dbf, and the system's allergy classification information, in data file class.dbf, all described in Table 2.) The system also builds a list (the "allergy list") of the allergy drugs and allergy categories known to the system (as in window 216). The elements in the allergy list include the same information as in the patient drug list, except that there is no drug name or drug ID for entries that were made as allergy category entries. (Information in the data files described in Table 2 is used to build these lists.)

Then, for each entry in the patient drug list, the system performs the following steps to determine which allergy messages, if any, the system should display. If the patient drug list drug (the "patient drug") is the same as an allergy list drug, the system displays a message that the patient is allergic to the drug. If the patient drug is in an allergy class and that allergy class is the allergy class of any drug in the allergy list, the system displays a message that the drug in the allergy list is in the allergy class and may show allergic cross-reactivity to the patient drug. Finally, if the allergy category to any depth (including sub-and subsub-categories) of the patient drug matches the corresponding category in any entry in the allergy list, the system displays a message that the patient is allergic to the drug (if the allergy list entry is a drug) or to the allergy category (if the allergy list entry's drug field is empty) and may show allergic cross-reactivity to the patient drug.

For example, if the index drug is acyclovir, if the patient is on one concomitant drug, ampicillin, and if the user has entered as drug allergies acyclovir, cephalosporins, and didanosine, then the system reports:

This patient is allergic to cephalosporins. Ampicillin is a penicillin and may show allergic cross-reactivity to cephalosporins.

This message is generated because the data file alrgdr.dbf shows that the concomitant drug ampicillin is in the allergy category penicillin, which may show allergic cross-reactivity to cephalosporins, which is shown in the data file class.dbf. The system also reports:

This patient is allergic to acyclovir.

This message is generated because acyclovir is the index drug and an allergy drug.

Pregnancy and Lactation. Pregnancy and lactation information is present and accessible for all drugs. If the patient is a female of child-bearing age, the system highlights the Pregnancy and Lactation function buttons to remind the user to review the information. The Pregnancy button will be highlighted (for example, with different colors) in a way that indicates a pregnancy classification for the drug. The FDA (U.S. Food and Drug Administration) pregnancy classification is a classification that may be used. There are five commonly-used FDA pregnancy classifications for drugs—classes A, B, C, D and X—and the letters may be displayed in the button to provide immediate information to the user. Both pregnancy and lactation information are displayed the way side effects are, containing level one and level two information. As with side effects, the system will display citations to references for both levels. The pregnancy and lactation information is stored in the data files preg.dbf, preg2.dbf, lact.dbf, and lact2.dbf (described in Table 1).

Warnings. The user selects the Warnings function button to display warnings, precautions and contraindications for the index drug. In response, the system assembles and displays the warning text from the data file warn.dbf (described in Table 1), in the same way that dosage texts are assembled and displayed. As with dosage, the system will display citations to references for the Warnings information.

Orders/Prescriptions. The system may be used to order drugs for in-patients and generate prescriptions for out-patients. If a drug has been expertly dosed when the user requests a prescription, the system displays the recommended dose along with the condition being treated. If a range of doses is recommended, the user is prompted to select a dose. The user can change any part of the resulting prescription, and any changes to the system's recommendations are noted on the print-out. Print-outs of orders contain both the actual prescription and the patient information used to generate the system-determined dosage.

Turning to FIG. 11, the system can generate in-patient drug orders (for brevity, "orders"). Orders are prescriptions for a patient that are directed to the pharmacy of the institution (e.g., hospital or clinic) in which the patient is receiving care. Users of the system can review previous orders, generate new orders, and sign off on outstanding orders.

When the user invokes the main window 200 menu option Orders, the system requires the user to enter a name and password combination, which determines what functions the user can perform. The user with "review only" permission is only allowed to review pervious orders. The user with "sign off" permission is only allowed to sign off on orders and to review previous orders. (The sign off identifies the person who signed off on the order, signifying that the person (e.g., nurse) taking care of the patient has seen the order.) The user with full permission is allowed to create new orders, to sign off on orders, and to review previous orders. No user is allowed to change a previous order. (To effect a change, the user will enter a new order to discontinue a previous order and then enter a new order.)

When the name and password have been accepted, the system presents the user an orders window 310 showing (if known to the system) or requesting (if not known to the system) the patient name, ID, age, and location in the institution, the current date and time, and a list of the patient's previous orders. If the patient records can be obtained, the system displays the patient's previous orders in previous orders area 312. Unless the patient is receiving drugs from a source other than the institution's pharmacy, all the patient's concomitant drugs will be displayed in previous orders area 312. The default form of display of previous orders shows all orders, sorted in ascending date-time order. The user may limit display to active orders only. The user may also display orders in descending date-time order or by physician.

Through orders window 310 the user can enter new orders and use function buttons to view and modify order-related information. The user may also employ the function buttons already described to invoke other features of the system, including Pharmacology, Side Effects, Cost, $Comparison, Interactions, Allergy, Pregnancy, Lactation, Warning, and (from the main menu bar) References.

When the user presses add button 314, the system displays a list of drugs and categories from which the user may choose a drug to be ordered. The system may be configured to display all drugs or only those drug's available in the formulary. After a drug is chosen, the system determines whether a knowledge base for the drug exists. If one exists, the system asks the user whether the drug should be expertly dosed. If so, the system runs the drug's knowledge base to dose the drug. When the knowledge base has been run, the new order is added to the current orders list and displayed in a cyan background color to indicate expert dosing. (As with all orders in the current orders list, this new order may be modified or deleted prior to being sent to the pharmacy.)

If no knowledge base exists or the user does not request expert dosing, the system presents to the user a list of "standard" formulary dosage recommendations, if any are known. The recommendations known to the system are in the data file FrmStDose.dbf. The user is required to select one, which the user may then edit in an add/change order window. If the user has selected one of the standard recommendations, the data entry fields in the add/change order window will be initialized to the recommendation's values; otherwise, the data entry fields will be blank. The user may use the add/change order window to enter or edit the order in any respect, including when the drug should be given, whether a generic substitute is acceptable, the route of administration, the dose amount, the dose form, and the frequency of administration. To assist the user, the system can display the routes (e.g., intravenous or oral) associated with the drug, the dose amounts in which the drug is available in the formulary for a chosen route, the dose forms (e.g., capsules or pills) in which the drug is available in the formulary for a chosen route, and the frequencies of administration associated with the drug and a chosen route. The association of routes with drugs is made in the data file FrmRte.dbf; the associations of drugs and routes with dose amounts and dose forms are made in data files FrmDose.dbf and FrmDForm.dbf, respectively; and the association of routes and drugs with frequencies of administration is made in the data file FrmFreq.dbf. Each of the foregoing files contains a record for each available combination. (The data files relating to orders are described in detail in Table 2.) The user can also designate the priority of administration by use of the STAT button (give at once), the First Dose Now button (give first dose within a certain time), and the Make Prn button (give as needed). When the Make Prn button is chosen, the system presents a data entry field in which the user can enter the as-needed indication (e.g. "prn for pain"). To assist the user, the system can display the as-needed indications generally associated with the drug, which are in the data file FrmPrn.dbf. Although the system has data files containing routes, dose amounts, dose forms, and frequencies that are available or recommended, the system allows the user to enter any value in a data entry field, whether or not the value is found in the system's data files.

After the user has made the necessary choices and accepted the order, the order is displayed as a new current order in Current Order area 316. (Current orders are orders that have been accepted by the user but not yet sent to the pharmacy. The user may change or delete a current order before it is sent.) At the same time, the system also adds the drug in the new current order to the patient's concomitant drug list. When added to the set of current orders, the new order is the selected order, and the system performs the following steps (which it performs for whichever one of the orders in Current Order area 316 is selected). The drug of the selected order is used as the (temporary) index drug and the processes already described are invoked to set the highlighting of the Side Effects, Interactions, Allergies, Pregnancy, Lactation, and Warning buttons, and all the function buttons may be used with respect to the selected order drug, which is used as the (temporary) index drug.

The user sends the current orders to the pharmacy by selecting Send button 318, in response to which the system transmits the orders to the pharmacy electronically (they are printed there as well) and adds them to the data files PatOrd.dbf and PatMedOrd.dbf. (The data files PatOrd.dbf and PatMedOrd.dbf are described in detail in Table 2.) Any orders expertly dosed and then changed by the user are flagged as such when stored in PatMedOrd.dbf. The date, time, and ordering physician for each order are also stored. The user is asked to confirm that he or she is satisfied with the current orders before the send operation is actually performed.

The user can use Change button 320 to change both a current order (one that has not been sent) or a previous order (one that has been sent). However, when a previous order is selected, the change operation actually creates a new order based on the previous one, and the previous order is not modified. To effect a modification of a previous order, the user selects the order in Previous Orders area 312 and selects Discontinue button 322. (When the user selects a previous order, the label displayed on Delete button 322 changes to "Discontinue".) In response, the system generates a new current order that is an order to discontinue the previous order. The user can delete this new order before it is sent but cannot edit it.

Citations to References. In response to a user request, the system displays citations to references pertinent to the information being displayed, as illustrated in FIG. 6. The references for each drug are tabulated in a data file, ref__cont.dbf, each record of which has a code indicating what the reference relates to—pharmacology, interaction, side effect, allergy, pregnancy, lactation, or warnings—and, when necessary, a keyword further qualifying the type of reference. The system uses the codes to select the pertinent references for display, depending on the context in which the user requests the display of references. The display will include any keywords for pharmacology and level one side effects, to indicate which drug interaction or side effect the cited reference relates to. The file ref__cont.dbf has pointers into a second data file, ref__bas.dbf, that contains full citations for each reference, which the system assembles and displays in response to the user's request. (Data files ref__bas.dbf and ref__cont.dbf are described more fully in Table 1.)

Organization of Data. Data used by the system is stored in data files and data index files. Storage of the files may be on direct access file media directly connected to the computer on which the system's programs execute, or they may be distributed, over a network or otherwise. The data and index files may be created on a personal computer using a database management system such as dBASE IV. (DBASE is a registered trademark of, and the dBASE product is available from, Borland International, Inc. of Santa Cruz, Calif.)

The system uses a separate directory for each drug (considered generically), named with the unique identification code assigned the drug, e.g., D00001. This directory contains the drug's knowledge base and the drug's data files. The drug knowledge bases are described later. The data files are listed and described in Table 1.

In addition, a separate directory contains data files and internally-created index files that are common to the system. These files are described in Table 2.

TABLE 1

| Name of file | |
|---|---|
| (Description of file) | |
| Data field | Description of data field |
| adr__txt.dbf | |
| (Top-level text for adverse reactions/side effects) | |
| Drug__ID | char len 6: unique identifier of drug (redundant because files in Table 1 are in drug-specific directories whose names are derived from Drug__ID) |
| Syst__ID | char len 2: unique identifier of physiologic system |
| Seq | char len 2: sequence number ordering the text blocks when the field Text has more than 254 characters |
| Text | char len 254: text describing side effects about specific physiologic system Syst__ID. This text may contain variables, which are names embedded in curly braces ("{ }"), which may be replaced by patient-specific text from the file out__text.dbf. |
| adr2__txt.dbf | |
| (Text for level 2 side effects) | |
| Drug__ID | (as above) |
| Syst__name | char len 30: name of physiologic system |
| Syst__ID | (as above) |
| Seq | (as above) |
| Text | char len 254: top-level text for level two information for specified Syst__name. |
| dose__txt.dbf | |
| (Top-level text for dosage) | |
| Drug__ID | (as above) |
| Seq | (as above) |
| Text | char len 254: top-level information about dosage. This text may contain variables (which relate to Text__ID in xref__dos.dbf and out__text.dbf) embedded in "{ }". These variables may be replaced by patient specific information from out__text.dbf or from the knowledge base. |
| phgy__txt.dbf | |
| (Top-level text for pharmacology/pharmacokinetics) | |
| Drug__ID | (as above) |
| Seq | (as above) |
| Text | char len 254: top-level information about pharmacology. This text may contain variables (which relate to Text__ID in xref__phm and out__text.dbf) embedded in "{ }". These variables may be replaced by patient specific information from out__text.dbf or from the knowledge base. |

TABLE 1-continued out_text.dbf
(Fill-in text for adr_txt.dbf dose_txt dbf, and phgy_txt.dbf)
Drug_ID      (as above)
Text_Ref     char len 5: unique name of the piece of text. The first letter means: S for
             side effects, T for dose or pharmacology
Text         Char len 254: the fill-in text information about side effects, dose, or
             pharmacology.
cost.dbf
(Cost for each form and unit of the drug and pointer to formula used to calculate cost.)
Drug_ID      (as above)
Brand_ID     num len 2: unique ID of the trade-name of the drug (00 if it is generic)
Dose_form    char len 15: text stating form of administration (e.g., "oral")
Unit         char len 5: text of unit ofdose (e.g., "mg")
Dose         num len 7.2: size of dose (e.g, 200.00 if drug comes in 200 mg. tablets)
Cost         num len 7.2: cost (a number for use in the cost calculation)
Formula      num len 3: index that selects (identifies) formula to be used to calculate
             cost of daily administration of the drug described in present record
Text         char len 50: x_daily statement
ref_bas.dbf
(Citations to references)
Ref_ID       char len 7: unique system-wide identifier of the reference
Author       char len 150: name(s) of the author(s)
Title        char len 254: title of the article
Journal      char len 80: journal in which the article appeared
Year         char len 11: year of publication
Volume       char len 20: journal volume number
Pages        char len 20: the numbers of the pages
ref_cont.dbf
(Reference information, pointers, and keywords)
Drug_ID      char len 6: unique identifier of the drug in whose directory the file
             ref_bas.dbf contains the entry for reference Ref_ID (may be same as, or
             different from, present drug directory)
Ref_ID       (as above)
React_ID     char len 1: the subject of the article, namely, 1 for side effects, 2 for drug
             interactions, 3 for pharmacology, 4 for allergy, 5 for pregnancy, 6 for
             lactation, 7 for warning, and 0 for unknown. For multiple subjects, there
             will be multiple records in this file.
Key          char len 45: for side effects, the name of physiologic system; for drug
             interaction, the name of the other drug; and for pharmacology, a
             pharmacologic parameter
xref_adr.dbf
(Pointers to out_text.dbf for each patient case for side effect variables)
Drug_ID      (as defined above for adr_txt.dbf)
Case         char len 4: number of the patient case
Text_ID      char len 3: unique identifier for piece of text about side effects; the first
             letter is always A. This corresponds to variable names embedded in
             adr_txt in "{ }" and allows such variables to be used as pointers into this
             file.
Text_Ref     char len 5: unique name of piece of text; the first letter is always S. This
             is a pointer into file out_text.dbf
xref_dos.dbf
(Pointers to out_text.dbf for each case for dosage variables)
Drug_ID      (as above)
Case         (as above)
Text_ID      char len 3: unique identifier for piece of text about dosage; the first letter
             is always D. This corresponds to variable names embedded in dose_txt in
             "{ }" and allows such variables to be used as pointers into this file.
Text_Ref     char len 5: unique name of piece of text. The first letter is always T. This
             is a pointer into file out_text.dbf.
xref_phm.dbf
(Pointers to out_text.dbf for each case for pharmacology variables)
Drug_ID      (as above)
Case         (as above)
Text_ID      char len 3: unique identifier for piece of text about pharmacology. The
             first letter is always P. This corresponds to variable names embedded in
             adr_txt in "{ }" and allows such variables to be used as pointers into this
             file.
Text_Ref     char len 5: unique name of the piece of text. The first letter is always T.
             This is a pointer into file out_text.dbf.
xref_prg.dbf
(Pointers to out_text.dbf for each case for pregnancy variables)
Drug_ID      (as above)
Case         (as above)

TABLE 1-continued

| | |
|---|---|
| Text_ID | char len 3: unique identifier for piece of text about pregnancy. This corresponds to variable names embedded in dose_txt in "{ }" and allows such variables to be used as pointers into this file. |
| Text_Ref | char len 5: unique name of piece of text. The first letter is always T. This is a pointer into file out_text.dbf. | xref_lac.dbf
(Pointers to out_text.dbf for each case for lactation variables)

| | |
|---|---|
| Drug_ID | (as above) |
| Case | (as above) |
| Text_ID | char len 3: unique identifier for piece of text about lactation. This corresponds to variable names embedded in dose_txt in "{ }" and allows such variables to be used as pointers into this file. |
| Text_Ref | char len 5: unique name of piece of text. The first letter is always T. This is a pointer into file out_text.dbf. | xref_wng.dbf
(Pointers to out_text.dbf for each case for warnings variables)

| | |
|---|---|
| Drug_ID | (as above) |
| Case | (as above) |
| Text_ID | char len 3: unique identifier for piece of text about warnings. This corresponds to variable names embedded in dose_txt in "{ }" and allows such variables to be used as pointers into this file. |
| Text_Ref | char len 5: unique name of piece of text. The first letter is always T. This is a pointer into file out_text.dbf. | xref_cst.dbf
(Dosage amount, unit, form, frequency and pointer to text for frequency of administration, and flag indicating whether dose is calculated by the knowledge base for this patient case)

| | |
|---|---|
| Drug_ID | (as above) |
| Case | (as above) |
| Dose | num len 7.2: the dose of drug |
| Unit | char len 7: the unit of drug (e.g., "mg.") |
| Dose_form | char len 16: the form of the dose (e.g., "oral") |
| X_daily | num len 5.2: how many times a day the dose is administered |
| RX_ID | num len 4: pointer to text representation of X_daily (the "x_daily statement") in cost_rx.dbf |
| Use_KB | logic len 1: "Y" if Dose X_daily, and RX_ID are calculated by the knowledge base | preg.dbf
(Level 1 data about this drug and pregnancy)

| | |
|---|---|
| Drug_ID | (as above) |
| Syst_ID | (as above; will always be number for pregnancy) |
| Seq | (as above) |
| Text | char len 254: contains the information about pregnancy. | preg2.dbf
(Level 2 pregnancy data)

| | |
|---|---|
| Drug_ID | (as above) |
| Syst_name | (as above; value will always be pregnancy) |
| Syst_ID | (as above; value will always be number for pregnancy) |
| Seq | (as above) |
| Text | char len 254: top-level text for level two information for specified Syst_name. | lact.dbf
(Level 1 data about this drug and lactation)

| | |
|---|---|
| Drug_ID | (as above) |
| Syst_ID | (as above; value will always be number for lactation) |
| Seq | (as above) |
| Text | char len 254: contains the information about lactation. | lact2.dbf
(Level 2 lactation data)

| | |
|---|---|
| Drug_ID | (as above) |
| Syst_name | (as above; value will always be lactation) |
| Syst_ID | (as above; value will always be number for lactation) |
| Seq | (as above) |
| Text | char len 254: top-level text for level two information for specified Syst_name. | warn.dbf
(Level 1 text for contraindications and other warnings)

| | |
|---|---|
| Drug_ID | (as above) |
| Syst_ID | (as above; value will always be number for warning) |
| Seq | (as above) |
| Text | char len 254: text describing warnings for a drug. This text may contain variable names embedded in "{ }". These variables may be replaced by patient-specific text from out_text.dbf. |

(end of) Table 1

The files of Table 1 are placed in each drug's directory so that the system can quickly access the data. Also, this structure makes it easy to update drug information. Changes can be made to one drug's directory without affecting other drug directories.

The customer may install in each drug's directory a text file, the contents of which the system will display in the pharmacy notes area 212 of the main window 200 whenever the drug is selected as the index drug.

In addition to the files stored in individual drugs' directories, the system has data and index files that are common to the entire system. These files are listed and described in Table 2.

TABLE 2

Name of file
(Description of file)
Data fields        Descriptions of data fields
name_abc.dbf
(shows names and ID's of drugs, generic and brand ID's, flags stating whether the drug has a knowledge base in the system, whether the drug exists at customer's (user's) site, and category and subcategory ID's)
Category_ID    char len 2: identifier of a therapeutic category to which the drug belongs
Subcat_ID      char len 2: (same as above, for subcategory, or 00 if none)
Subsubcat_ID   char len 2: (same as above, for subsubcategory, or 00 if none)
Drug_ID        char len 6: unique ID of the generic form of the drug
Brand_ID       num len 2: unique ID of the trade-name of the drug (00 if it is generic)
Exists         logical: drug has a knowledge base in system
Cust_exists    logical: drug exists at customer's (user's) site
Name           char len 45: Name of the drug in text form
abc_all.ndx
(index file listing all drug names alphabetically)
Drug_number    integer 1: index count to unique drug names in file name_abc.dbf. (There may be more than one entry in name_abc.dbf for acyclovir, e.g., one for Category A, another for Category B.)
Drug_index     long 1: pointer to unique drug name in file name_abc.dbf.
abc_ext.ndx
(index file of only those drugs with knowledge bases in the system)
               (this file has same field structure as abc_all.ndx)
name_abc.ndx
(index file with first two letters tied to name_abc.dbf)
First2Letters  char 2: first two letters of drug names
Drug_index     long 1: pointer into name_abc.dbf to first drug whose name starts with the first two letters
name_abce.ndx
(index file with first two letters tied to name_abc.dbf for only those drugs with knowledge bases in the system
               (this file has same field structure as name_abc.ndx)
cat.ndx
(index to name_abc.dbf sorted in category order)
Category_ID    (as above)
Subcat_ID      (as above)
Subsubcat_ID   (as above)
Drug_index     long 1: pointer to entry in name_abc.dbf corresponding to category/sub-category/subsubcategory.
cate.ndx
(index to name_abc.dbf sorted in category order for only those drugs with knowledge bases in the system)
               (this file has same field structure as cat.ndx)
scat.ndx
(index to name_abc.ndx sorted in subcategory order)
               (this file has same field structure as cat.ndx)
scate.ndx
(index to name_abc.ndx sorted in subcategory order for only those drugs with knowledge bases in the system)
               (this file has same field structure as cat.ndx)
sscat.ndx
(index to name_abc.ndx sorted in subsubcategory order)
               (this file has same field structure as cat.ndx)
sscate.ndx
(index to name_abc.ndx sorted in subsubcategory order for only those drugs with knowledge bases in the system)
               (this file has same field structure as cat.ndx)
categ.dbf
(category names)
Category_ID    (as above)
Subcat_ID      (as above)
Subsubcat_ID   (as above)
Name           char len 55: when Subcat_ID is 0, the name of category; otherwise, when Subsubcat_ID is 0, the name of subcategory; otherwise, the name of subsubcategory

TABLE 2-continued

| | |
|---|---|
| Therapy | char len 1: "1", if the category should be shown by the system as a category of drugs from which the user may choose the index drug; "0", if not |
| ctgr.ndx | |
| (index to categ.dbf file for all categories of drugs (tells number of drugs in each category)) | |
| ctgre.ndx | |
| (index to categ.dbf file for only those categories of drugs with knowledge bases in the system (tells number of drugs known to the system for each)) | |
| alrgdr.dbf | |
| (allergy categories in which a drug falls) | |
| Categor_ID | char len 6: allergy category ID (composite of three two-character fields including a subcategory and a subsubcategory, as in name_abc.dbf) |
| Drug_ID | char len 6: (as above) |
| alrgnm.dbf | |
| (names of allergy categories) | |
| Categor_ID | char len 6: (as above) |
| Name | char len 55: allergy category name |
| class.dbf | |
| (data file of the allergy classes, which are groupings of categories in which all drugs show allergic cross-reactions) | |
| Class_ID | char len 3: unique identifier of the class |
| Subclass | char len 3: a sequence number for multiple full Categories in the same Class_ID |
| Categor_ID | (as above) |
| condrg.dbf | |
| (data file of all drugs with FDA approval and also, preferably, all drugs that are commonly used for treating the condition) | |
| Drug_ID | (as above) |
| Condition | char len 55: text name of condition |
| condrg.ndx | |
| (index file into names_abc.dbf on drugs and conditions) | |
| generic.ndx | |
| (index to names_abc.ndx to only the generic drug names) | |
| clsnm.ndx | |
| (index to categ.dbf file sorted in category_ID, subcategory_ID, and subsubcategory_ID order) | |
| cost_rx.dbf | |
| (data file containing RX_Id's and corresponding text for daily recommended dosage) | |
| RX_ID | num len 6: unique number of x_daily statement. |
| Text | char len 50: the x_daily statement (text stating frequency of administration). |
| drug_int.dbf | |
| (data file containing drug interactions) | |
| Drug | char len 61: the name of one drug (ended by "#") or the names of two drugs (separated by "&"). |
| Seq | (as above) |
| Text | char len 254: contains information about drug interactions between the two drugs, if there are two, or about interaction effects of the one drug. |
| Type | char len 1: the type of drug interaction: mild, moderate, major, or unknown. |
| PatOrd.dbf | |
| (patient order records) | |
| PatientID | char len 10: unique patient identifier |
| OrderNum | char len 3: order number |
| Date | char len 8: date order was placed |
| Time | char len 4: time order was placed |
| Location | char len 20: location of the patient |
| HealthID | char len 10: ID of physician who made the order |
| PatMedOrd.dbf | |
| (patient orders) | |
| PatientID | (as above) |
| OrderNum | (as above) |
| Sequence | char len 3: medication order sequence number |
| DrugName | char len 45: name of drug being ordered |
| Drug_Id | char len 6: system drug ID or formulary drug ID (blank if there is none) |
| FormId | char len 10: unique institution formulary drug identifier. |
| Dose | char len 7.2: dose size |
| Unit | char len 5: dose unit (e.g. mg.) |
| Route | char len 16: route the drug is to be administered (e.g., "oral") |
| Form | char len 16: form of the drug (e.g., tablets) |
| Freq | char len 50: daily frequency of administration (e.g., 3 times a day) |
| ExpDosed | char len 1: "Y" means yes, order was expertly dosed; "N" means it was not; and "C" means it was but the dosing was changed by user |
| Priority | char len 1: priority of administration: "S" for "stat"; "F" for "first dose now" |
| Prn | char len 80: text, if drug is to be administered as needed, describing condition (e.g., "for pain", "temp > 100") |

TABLE 2-continued

```
Disc          char len 1: "D" if drug order is discontinued
SignOff       char len 10: ID of person who acknowledged order
Frmlry.dbf
(cross reference system drug ID to formulary drug ID)
Drug_Id       char len 6: (as above, unique system drug identifier)
FormId        char len 10: unique institution formulary drug identifier.
FrmRte.dbf
(formulary routes)
FormId        (as above)
Route         (as above)
FrmDose.dbf
(formulary doses and units)
FormId        (as above)
Route         (as above)
Dose          (as above)
Unit          (as above)
FrmDForm.dbf
(formulary doses and dose forms)
FormId        (as above)
Route         (as above)
Form          (as above)
FrmFreq.dbf
(formulary drug frequencies)
FormId        (as above)
Route         (as above)
Freq          (as above)
FrmPrn.dbf
(formulary as needed statements)
FormId        (as above)
Prn           char len 80: the associated "as needed" statement.
                      (end of) Table 2
```

Decision trees and the patient "case". In developing knowledge bases for drugs in the system, it is useful to create for each drug a decision tree based on the factors that are important in determining proper dosage of the drug. As illustrated in FIGS. 12–22, the decision tree can be written as a row and column matrix, where the columns represent factors and the rows represent distinct patient cases, with accompanying text describing proper dosing for the various cases. Such a decision tree shows the factors used to determine proper dosage of a drug and relates the factors to particular dosage determinations.

Although any number of factors may be included and programmed into a drug's knowledge base, the following factors are routinely used in the system: therapy type (active versus prophylaxis treatment), condition, subcondition, dosage form (oral, intravenous, and so on), age, creatinine clearance range, dialysis type, and liver disease.

Each row in a drug's decision tree matrix is a unique combination of column values and therefore represents the unique patient "case" where those values are present. Each case has associated with it (in the system's data files and the drug's knowledge base) values, calculations, and pieces of text specific to the patient's situation that will be included in the system's information displays.

For ease of calculation in the knowledge base, each possible setting for a particular column in a drug's decision tree is assigned a distinct value so that the case for each set of clinical conditions can be calculated simply by adding the values across the row. The values in Table 3, as applied to the decision tree matrix illustrated in FIGS. 12–22, are illustrative. For each row, the row number and the case number are equal to each other and to the sum of the column values.

FIGS. 12–22 show an illustrative decision tree for acyclovir. The factors important for dosing acyclovir are condition, subcondition, dosage form, dialysis type, CrCl range, and liver disease. The first row is case 1, where the patient has a herpes simplex infection, mucocutaneous immunocompromised host, no dialysis, good kidney function (a CrCl of 80 ml./min. or higher), no liver disease, and the doctor selects intravenous therapy. As shown in FIG. 17 (Cases 1–4), the dosage recommended for case 1 is calculated based on the patient's weight, namely 5 mg. per kilogram, every 8 hours. This value is rounded to the nearest 25 mg. in the acyclovir knowledge base because intravenous acyclovir is available in multiples of 25 mg. Case 15 is for the same patient as case 1, only for oral therapy rather than intravenous, and the dosage is 200 mg. 5 times a day. (FIG. 17) For case 19, where the patient has moderate kidney dysfunction (CrCl is between 25 and 50 ml./min.), the dose is 200 mg. reduced to 3 times a day. Because oral acyclovir is available only in 200 and 800 mg. tablets, the recommended dose will be 200 mg., 800 mg., or some multiple of those amounts.

TABLE 3

|  | Value |
|---|---|
| Condition | |
| Herpes Simplex | 0 |
| Herpes Zoster (Varicella zoster) | 70 |
| Other | 98 |
| Subcondition | |
| Mucocutaneous immunocompromised host | 0 |
| Mucocutaneous immunocompetent host | 14 |
| Prophylaxis | 28 |
| Encephalitis | 56 |
| Dosage Form | |
| Intravenous | 0 |
| Oral | 14 |
| Dialysis Type | |
| None | 0 |
| Hemodialysis | 10 |
| Peritoneal Dialysis | 12 |

TABLE 3-continued

| | Value |
|---|---|
| CrCl Range | |
| >=80 | 0 |
| 50–80 | 2 |
| 25–50 | 4 |
| 10–25 | 6 |
| <10 | 8 |
| Liver Disease | |
| No | 1 |
| Yes | 2 |

Drug knowledge base. The system incorporates decision tree information in the data files, which have already been described, and the drug knowledge bases, which will now be described.

A drug's knowledge base includes a collection of rules representing the drug's decision tree, including rules to do any necessary calculations, as well as rules to interact with the C portion of the system. When executed by its expert system shell, the knowledge base calculates the patient case, requesting information when necessary.

Top-level knowledge base. As a prelude to the further description of drug knowledge bases, the top-level knowledge base will be described. The top-level knowledge base defines the properties, classes, objects, slots and rules that are common to, and joined to, all individual drug knowledge bases.

The top-level knowledge base has one rule, SetCaseKnown, that is the last rule to fire when a patient case has been determined. This rule calls the C function "SetCaseKnown" to set the case number global variable, and then calls the C function "assembleTxt". The function assembleTxt performs the steps of assembling text and substituting variables that have already been described.

The top-level knowledge base has two classes, DrugFillInClass and Calc_Dose, that define properties whose values the C portion of the system may obtain by calling the expert system shell. The class Calc_Dose is used to hold calculated doses to be passed to the C functions that use this information. The class Calc_Dose has five properties:

| | |
|---|---|
| FDose | the calculated dose as a floating point number; |
| IDose | the calculated dose as an integer; |
| IsInteger | boolean, true if dose is integer; |
| Freq | floating point number indicating frequency of administration (times per day); and |
| RX_Daily | text containing same information as Freq. |

The class DrugFillInClass is used for objects that pass information to the C function assembleTxt. It defines the following two properties:

| | |
|---|---|
| Text | holds patient- and case-specific text to be inserted; and |
| Var | identifies the text variable Text belongs to. |

Objects of class DrugFillInClass include Dose_Fill_In. In a drug knowledge base, Dose_Fill_In.Text will be set to a string representing the dose amount(s), for example, "200 to 300", and Dose_Fill_In.Var will be set to the corresponding variable name, for example, "D01", so that in assembleTxt the variable {D01} will be replaced with the string representing the dose amounts.

The top-level knowledge base also defines the following objects:

| | |
|---|---|
| xxxx_Found | hypotheses used to determine if various stages of processing are complete; |
| xx_Num | integers each holding the value assigned to a column of the decision tree, e.g., COND_Num for the clinical condition and CrCL_Num for creatinine clearance (these are the values summed to calculate the case); and |
| Pt | the patient object, described in the following paragraph. |

The object Pt represents the patient. It includes the following properties:

| | |
|---|---|
| Age | the patient's age in years; |
| Case | text representation of the patient case; |
| COND | condition being treated; |
| CrCl | creatinine clearance; |
| DF | selected dosage form of the drug; |
| Drug | name (text) of the drug; |
| Drug_ID | unique drug identifier; |
| IBW | patient's ideal body weight in kg. |
| ICase | integer representation of the patient's case; |
| ID | the patient's identification number; |
| LD | boolean: true if patient has liver disease; |
| LD_Type | severity of the liver disease; |
| SCr | patient's serum creatinine value; |
| TX | therapy type; and |
| Wt | patient's actual body weight in kilograms. |

Drug knowledge base. In the system, drug knowledge bases are specific to each individual drug. To illustrate the implementation of drug knowledge bases, an implementation of a drug knowledge base for acyclovir based on the decision tree of FIGS. 12–22 will now be described.

When any drug knowledge base is invoked, the C program suggests the hypothesis Done as the hypothesis to be proved. This hypothesis is proved by the rule Analysis_Completed, which is a "trigger" rule designed to start the process. Rule Analysis_Completed for the drug acyclovir may be expressed (in a C-like notation) as follows:

```
RULE Analysis_Completed
IF
        Valid_Patient           &&
        COND_Found              &&
        SUB_COND_Found          &&
        DF_Found                &&
        DIALYSIS_Found          &&
        CrCl_Found              &&
        LD_Found                &&
        Case_Found              &&
        Dose_Index_Found        &&
        Dose1_Found             &&
        Terminate
THEN ASSERT
        Done
END
```

The semantics require that for rule Analysis_Completed to prove Done, all of its conditions (the boolean expressions after IF) must be proved in the order in which they are listed.

The first condition, hypothesis Valid_Patient, is proved in rule Standard_Patient_Information. Rule Standard_Patient_Information is a rule that always fires when execution of the knowledge base begins. It puts the name of the drug into the Pt.Drug slot and creates the fill-in text objects for the patient's creatinine clearance and serum creatinine.

The next condition, hypothesis COND_Found, is proved in rules of the form COND_xxx, which are fired when proving the COND_Found hypotheses. If the patient's condition matches the condition such a rule is looking for, the corresponding value is assigned to COND_Num.Inum. This is illustrated in the following example.

RULE COND_Herpes_Zoster_Varicella_zoster
IF
   Pt.COND=="Herpes Zoster (Varicella-zoster)"
THEN ASSERT
   COND_Found
AND DO
   COND_Num.INum=70;
   SUB_COND_Num.INum=0;
   SUB_COND_Found=true;
END This rule illustrates that for certain conditions, the subcondition is determined when the condition is known, so SUB_COND_Found can be set to true without firing a subcondition rule. (The condition numbers (the condition column values) in the examples—70 for Herpes Zoster (Varicella-zoster) and 56 for Herpes Simplex Encephalitis—and other parameters of these example rules will come from the acyclovir decision tree in FIGS. 12–22 and from Table 3.)

The next condition of rule Analysis_Completed, hypothesis SUB_COND_Found, may be proved in the rule for the condition, as it is in the foregoing example. It may also be proved in its own rule, as in the following example, the rule for the Herpes Simplex subcondition Encephalitis. The following example also illustrates that the condition or subcondition may also determine the dosage form:

RULE SUB_COND_Encephalitis
IF
   Pt.SUB_COND=="Encephalitis"
THEN ASSERT
   SUB_COND_Found
AND DO
   SUB_COND_Num.INum=56;
   DF_Num.INum=0;
   DF_Found=true;
   Pt.DF="Intravenous";
END If the condition, Pt.COND, or the subcondition, Pt.SUB_cond, is unknown when the knowledge base attempts to prove COND_Found or SUB_COND_Found, a metaslot function on Pt.COND or Pt.SUB_COND is invoked to obtain the clinical condition or subcondition from the user. (Metaslots define C functions that are called when a value for a property (slot) that is required to evaluate a condition of a rule is unknown at the time the rule is considered for firing.) In this case, the metaslots Pt.COND and Pt.SUB_COND are handles for C function used to determine a value for the COND and SUB_COND slots, respectively, of the Pt object.

The next condition of rule Analysis_Completed, hypothesis DF_Found, is proved in rules of the form DF_xxx, which assign the appropriate value for the selected dosage form, as in the following example.

RULE DF_Intravenous
IF
   Pt.DF=="Intravenous"
THEN ASSERT
   DF_Found
AND DO
   DF_Num.INum=0;
END If Pt.DF is not known when this rule is fired, the metaslot function for the slot Pt.DF is run to request the user to select the dosage form.

The next condition of rule Analysis_Completed, the hypothesis DIALYSIS_Found, is proved by rules of the form DIAL_TYPE_xxx, which assign values based on the type of dialysis (or "none") the patient is on, as in the following example.

RULE DIAL_TYPE_Peritoneal_Dialysis
IF
   Pt.DIAL_TYPE=="Peritoneal Dialysis"
THEN ASSERT
   DIALYSIS_Found
AND DO
   DIALYSIS_Num.INum=12;
   CrCl_Found=true;
   CrCl_Num.INum=0;
END For a patient on dialysis the system considers creatinine clearance meaningless and therefore forces its values as shown.

The next condition of rule Analysis_Completed, hypothesis CrCl_Found, is proved by rules of the form CrCl_xxx, which determine the value assigned for the patient's creatinine clearance, as in the following example.

RULE CrCl_25_50
IF
   Pt.CrCl<50 &&
   PT.CrCl>=25
THEN ASSERT
   CrCl_Found
AND DO
   CrCl_Num.INum=4;
END The next condition of rule Analysis_Completed, hypothesis LD_Found, is proved in rules LD_True and LD_False, which assign the values 2 or 1, respectively, to LD_Num.Inum for cases where the patient does, or does not, have liver disease, as in the following example.

RULE LD_True
IF
   Pt.LD
THEN ASSERT
   LD_Found
AND DO
   LD_Num.INum=2;
END

The next condition of rule Analysis_Completed, hypothesis Case_Found, is proved by the rule Find_Case. In the present example acyclovir knowledge base, the rule is:

RULE Find_Case
IF

| | |
|---|---|
| COND_Found | && |
| SUB_COND_Found | && |
| DF_Found | && |
| DIALYSIS_Found | && |
| CrCl_Found | && |
| LD_Found | |

THEN ASSERT
   Case_Found
AND DO
   Pt.ICase=COND_Num.INum
     +SUB_COND_Num.INum
     +DF_Num.INum
     +DIALYSIS_Num.INum

```
        +CrCl_Num.INum
        +LD_Num.INum;
    Pt.Case=Integer_to_string (Pt.ICase);
END
```
The proving of the condition hypotheses of this Find_Case rule has already been described. The order of the conditions in this rule is important, because the rules invoked to prove the earlier conditions must fire before the knowledge base attempts to prove the later conditions in this rule. For example, in proving COND_Found, the clinical condition becomes known, and from that the subcondition may be determined, in which case SUB_COND_Found is already proved. Some clinical conditions determine the form of the drug to be used, in which case DF_Found is also already proved. If the order of conditions in this rule were reversed, the system would request the user to provide dosage form and subcondition information in inappropriate situations.

When all its conditions are met, the Find_Case rule sums the values assigned to the choices (COND_Num.Inum, SUB_COND_Num.Inum and so forth) to calculate the patient's case (Pt.ICase).

The hypothesis Dose_Index_Found is set true in rule DoseIndex_NotNeeded_-Oral_Cases and in rules of the form DoseIndex_For_Case_xxx. In the present example, rule DoseIndex_NotNeeded_Oral Cases proves the Dose1_Found hypothesis for all patient cases where the dosage form is oral:

```
RULE DoseIndex_NotNeeded_Oral_Cases
IF
    Case_Found &&
    Pt.DF=="Oral"
THEN ASSERT
    Dose1_Found
AND DO
    Dose_Index_Found=false;
END
```

By asserting Dose1_Found, this rule indicates that the calculation process is complete and all associated Calc_Dose and Text_Fill_In objects have been created. The knowledge base does not have to perform calculations for oral doses of acyclovir.

For intravenous doses of acyclovir, on the other hand, the knowledge base does perform calculations, and they are performed in rules of the form DoseIndex_For_Case_xxx. In the present example, for cases 1 through 4, the rule is:

```
RULE DoseIndex_For_Case_1_4
IF
```

| Case_Found | && |
| Pt.ICase >= 1 | && |
| Pt.ICase <= 4 | |

```
THEN ASSERT
    Dose_Index_Found
AND DO
    DoseIndex.D1=25 * round ((Pt.IBW* 5)/25);
    DoseIndex.D2=0;
    DoseIndex.Freq=3;
    DoseIndex.RX_Daily="every 8 hours";
END
```

This rule uses an object, DoseIndex, which is defined in the acyclovir knowledge base. The slots of DoseIndex include D1 and D2, numbers used to hold a dose (if D2 is zero) or to hold a range of doses (otherwise); Freq, the number of times a day the dose is to be administered; and RX_Daily, the English text version of Freq. The dosage calculations in these rules are based on Pt.IBW, the patient's ideal body weight in kilograms. The dose for intravenous acyclovir is rounded to the nearest 25 mg. because intravenous acyclovir is available in multiples of 25 mg.

The next hypothesis in the conditions of rule Analysis_Completed is Dose1_Found. Dose1_Found is asserted when the calculation process is complete and all associated Calc_Dose and Text_Fill_In objects have been created. Dose1_Found is proved in rule DoseIndex_NotNeeded_Oral_Cases (described above) and in rules Dose2_is_0, Dose1_The_Same, and Dose1_Different. The former two rules are for the situation where only one dose (not a range) has been calculated. Rule Dose1_The_Same is illustrative:

```
RULE Dose1_The_Same
IF
```

| Dose_Index_Found | && |
| Pt.DF = "Intravenous" | && |
| DoseIndex.D1 = DoseIndex.D1 | |

```
THEN ASSERT
    Dose1_Found
AND DO
    Dose_Fill_In.Text=number_to_string
        (DoseIndex.D2);
    Dose_Fill_In.Var="D01";
    Create new object "CalculatedDose1" of class Calc_
        Dose;
    CalculatedDose1.IDose=DoseIndex.D1;
    CalculatedDose1.IsInteger=true;
    CalculatedDose1.RX_Daily=DoseIndex.RX_Daily;
    CalculatedDose1.Freq=DoseIndex.Freq;
END
```

The rule Dose1_Different applies when the calculated dosage is a range of values:

```
RULE Dose1_Different
IF
```

| Dose_Index_Found | && |
| Pt.DF = "Intravenous" | && |
| DoseIndex.D1 != DoseIndex.D2 | && |
| DoseIndex.D2 > 0 | |

```
THEN ASSERT
    Dose1_Found
AND DO
    Dose_Fill_In.Text=number_to_string
        (DoseIndex.D1);
    Dose_Fill_In.Text=strcat(Dose_Fill_In.Text,"to");
    Dose_Fill_In.Text=strcat(Dose_Fill_In.Text,
        number_to_string(DoseIndex.D2));
    Dose_Fill_In.Var="D01";
    Create new object "CalculatedDose1" of class Calc_
        Dose;
    CalculatedDose1.IDose=DoseIndex.D1;
    CalculatedDose1.IsInteger=true;
    CalculatedDose1.RX_Daily=DoseIndex.RX_Daily;
    CalculatedDose1.Freq=DoseIndex.Freq;
    Create new object "CalculatedDose2" of class Calc_
        Dose;
    CalculatedDose2.IDose=DoseIndex.D2;
```

CalculatedDose2.IsInteger=true;
CalculatedDose2.RX__Daily=DoseIndex.RX__Daily;
CalculatedDose2.Freq=DoseIndex.Freq;
END The data in the objects of class Calc__Dose created in these rules are placed there for use in the C portion of the system, for example in cost calculation and display.

The last condition in rule Analysis__Completed is hypothesis Terminate, which is proved by rule End__Processing, which in the acyclovir knowledge base always fires and does nothing else. In other knowledge bases, this last rule may take actions to complete pending computations.

When Analysis__Completed proves Done, the processing in the drug's knowledge base is completed, so rule SetCaseKnown in the top-level knowledge base fires, calling the C functions SetCaseKnown and assembleTxt, as described above.

The Clinical Content. The clinical information incorporated in the drug knowledge bases and the data files may be derived from published references by physicians, pharmacologists, and librarians. Information may be gathered and kept current with online searches of the Medline database. (Medline is a database service of the National Library of Medicine, which may be accessed through the PaperChase® service of Beth Israel Hospital of Boston, Mass.) In doing so, researchers will generally search for articles indexed by drug name and the following keywords and phrases: drug interactions, side effects, and pharmacokinetics. Researchers may also run supplemental searches to find special-topic material.

The articles found for each drug may be catalogued in a computer database and reviewed by researchers, who decide whether or not to use them in creating a summary and decision tree for the drug. Summaries and decision trees may be reviewed and corrected, if necessary, by the members of a scientific advisory board. Citations to the sources of whatever information is incorporated into the system's drug knowledge base and system's data files may then be included in the references files ref_bas.dbf and ref_cont.dbf, described above.

We claim as our invention:

1. A method for creating an electronic prescription, comprising:
   interactively receiving an input from a user selecting a medication;
   displaying to the user alternative elements for creating an electronic prescription for the currently selected medication, including the routes associated with the medication, the dose amounts in which the medication is available in a formulary for a chosen route, the dose forms in which the medication is available in the formulary for a chosen route, and the frequencies of administration associated with the medications and a chosen route; and
   receiving from the user an input accepting an order including the user selected medication, frequency of administration, route of administration, dose amount, and dose form.

2. The method of claim 1, further comprising:
   interactively receiving an input from the user selecting when the medication should be administered, and whether a generic substitute is acceptable for the medication; and
   sending the order electronically to a pharmacy.

3. The method of claim 1, further comprising:
   determining which ordering alternatives to display to a user by accessing an electronic database of associations comprising an association of routes with medications, an associations of medications and routes with dose amounts, an associations of medications and routes with dose forms, and an association of routes and medications with frequencies of administration.

4. The method of claim 3, wherein the database of associations contains a record for each available combination.

5. The method of claim 3, wherein the order is represented by an electronic order record comprising:
   a name of the medication;
   a unique medication identifier;
   a medication dose size;
   a medication route of administration;
   a medication form; and
   a medication daily frequency.

6. A system for creating an electronic prescription for a patient, comprising:
   a user interface for interactively receiving an input from a user selecting a medication; and
   a database of associations configured to provide the user with alternative elements for creating an electronic prescription for the currently selected medication, the database comprising associations of routes with medications, associations of medications and routes with dose amounts, associations of medications and routes with dose forms, and associations of routes and medications with frequencies of administration.

7. The system of claim 6, wherein the database of associations contains a record for each available combination.

8. The system of claim 6, further comprising:
   means for determining which ordering alternatives to display to the user by accessing the database of associations.

9. The system of claim 6, further comprising:
   a user interface for interactively receiving from the user an input accepting an order including the user-selected medication, frequency of administration, route of administration, dose amount, and dose form.

10. The system of claim 9, further comprising:
    a user interface for interactively receiving from the user an input selecting when the medication should be administered, and whether a generic substitute is acceptable for the medication and an input causing the system to send the order electronically to a pharmacy.

11. The system of claim 10, wherein the order is represented by an electronic order record comprising:
    a name of the medication;
    a unique medication identifier;
    a medication dose size;
    a medication route of administration;
    a medication form; and
    a medication daily frequency.

12. A computer program product, tangibly stored on a computer-readable medium, for creating an electronic prescription for a patient, the product comprising instructions for causing a computer to:
    interactively receive an input from a user selecting a medication;
    display to the user alternative elements for creating an electronic prescription for the currently selected medication, including the routes associated with the medication, the dose amounts in which the medication is available in a formulary for a chosen route, the dose forms in which the medication is available in the formulary for a chosen route, and the frequencies of administration associated with the medications and a chosen route; and receive from the user an input accepting an order including the user-selected medication, frequency of administration, route of administration, dose amount, and dose form.

13. The product of claim 12, further comprising instructions to:

interactively receive an input from the user selecting when the medication should be administered, and whether a generic substitute is acceptable for the medication; and sending the order electronically to a pharmacy.

14. The product of claim 12, further comprising instructions to:

determine which ordering alternatives to display to a user by accessing an electronic database of associations comprising an association of routes with medications, an associations of medications and routes with dose amounts, an associations of medications and routes with dose forms, and an association of routes and medications with frequencies of administration.

15. The product of claim 14, wherein the database of associations contains a record for each available combination.

16. The product of claim 14, wherein the order is represented by an electronic order record comprising:

a name of the medication;

a unique medication identifier;

a medication dose size;

a medication route of administration;

a medication form; and a medication daily frequency.

* * * * *